United States Patent
Dye et al.

(10) Patent No.: US 7,976,549 B2
(45) Date of Patent: Jul. 12, 2011

(54) INSTRUMENTS FOR DELIVERING SPINAL IMPLANTS

(75) Inventors: Justin Dye, Mansfield, MA (US); Noelle Dye, Charlestown, MA (US); Dennis Colleran, North Attleboro, MA (US)

(73) Assignee: Theken Spine, LLC, Akron, OH (US)

( * ) Notice: Subject to any disclaimer, the term of this patent is extended or adjusted under 35 U.S.C. 154(b) by 761 days.

(21) Appl. No.: 11/690,692

(22) Filed: Mar. 23, 2007

(65) Prior Publication Data

US 2007/0225726 A1    Sep. 27, 2007

Related U.S. Application Data

(60) Provisional application No. 60/785,318, filed on Mar. 23, 2006, provisional application No. 60/825,084, filed on Sep. 8, 2006, provisional application No. 60/825,089, filed on Sep. 8, 2006.

(51) Int. Cl.
*A61B 17/58* (2006.01)
*A61B 17/60* (2006.01)
*A61F 2/00* (2006.01)

(52) U.S. Cl. .................................. 606/99; 606/86 A

(58) Field of Classification Search ................ 606/86 A, 606/99
See application file for complete search history.

(56) References Cited

U.S. PATENT DOCUMENTS

| | | | |
|---|---|---|---|
| 3,136,040 A | 6/1964 | Bauer | |
| 3,486,505 A | 12/1969 | Morrison | |
| 3,867,728 A | 2/1975 | Stubstad et al. | |
| 4,501,269 A | 2/1985 | Bagby | |
| 4,714,469 A | 12/1987 | Kenna | |
| 4,834,757 A | 5/1989 | Brantigan | |
| 4,863,477 A | 9/1989 | Monson | |
| 4,878,915 A | 11/1989 | Brantigan | |
| 4,904,261 A | 2/1990 | Dove et al. | |
| 4,997,432 A | 3/1991 | Keller | |
| 5,059,193 A | 10/1991 | Kuslich | |
| 5,171,278 A | 12/1992 | Pisharodi | |
| 5,390,683 A | 2/1995 | Pisharodi | |
| 5,484,437 A | 1/1996 | Michelson | |
| 5,554,191 A | 9/1996 | Lahille et al. | |
| 5,562,736 A | 10/1996 | Ray et al. | |

(Continued)

FOREIGN PATENT DOCUMENTS

WO    WO-9526164    10/1995

(Continued)

*Primary Examiner* — Thomas C Barrett
*Assistant Examiner* — Christine L Nelson
(74) *Attorney, Agent, or Firm* — Middleton Reutlinger; Robert H. Eichenberger; Chad D. Bruggeman

(57) ABSTRACT

A method, apparatus, and system are provided to place an insert in a space between boney structures. The insert may be rotatably coupled to the delivery instrument. The delivery instrument may comprise a body and an articulating member. The articulating member may slidably interact with the insert to rotate the insert about a pivot point. A first actuator is operatively coupled to the articulating member such that actuating the first actuator translates the articulating member relative to the body. An engagement member may be coupled to the body and adapted to releasably and rotatably secure the insert to the delivery instrument. The articulating member and the engagement member may be offset from each other in such a manner that when the articulating member engages the insert, the insert rotates relative to the delivery instrument. Alternatively, the insert may be coupled to the delivery instrument via rotatable attachment members.

16 Claims, 20 Drawing Sheets

U.S. PATENT DOCUMENTS

| | | |
|---|---|---|
| 5,653,762 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,449 A | 12/1997 | McKay |
| 5,713,899 A | 2/1998 | Marnay et al. |
| 5,716,415 A | 2/1998 | Steffee |
| 5,741,253 A | 4/1998 | Michelson |
| 5,749,916 A | 5/1998 | Richelsoph |
| 5,776,199 A | 7/1998 | Michelson |
| 5,782,830 A | 7/1998 | Farris |
| 5,797,909 A | 8/1998 | Michelson |
| 5,800,550 A | 9/1998 | Sertich |
| 5,860,973 A | 1/1999 | Michelson |
| 5,885,299 A | 3/1999 | Winslow et al. |
| 5,888,228 A | 3/1999 | Knothe et al. |
| 6,033,405 A | 3/2000 | Winslow et al. |
| 6,039,761 A | 3/2000 | Li et al. |
| 6,039,762 A | 3/2000 | McKay |
| 6,059,790 A | 5/2000 | Sand et al. |
| 6,074,423 A | 6/2000 | Lawson |
| 6,080,155 A | 6/2000 | Michelson |
| 6,093,207 A | 7/2000 | Pisharodi |
| 6,096,038 A | 8/2000 | Michelson |
| 6,123,705 A | 9/2000 | Michelson |
| 6,136,031 A | 10/2000 | Middleton |
| 6,143,032 A | 11/2000 | Schafer et al. |
| 6,156,037 A | 12/2000 | LeHuec et al. |
| 6,174,334 B1 | 1/2001 | Suddaby |
| 6,183,517 B1 | 2/2001 | Suddaby |
| 6,206,923 B1 | 3/2001 | Boyd et al. |
| 6,214,050 B1 | 4/2001 | Huene |
| 6,245,108 B1 | 6/2001 | Biscup |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Houfburg |
| 6,319,257 B1 | 11/2001 | Carignan et al. |
| 6,328,738 B1 | 12/2001 | Suddaby |
| 6,368,325 B1 | 4/2002 | McKinley et al. |
| 6,387,130 B1 | 5/2002 | Stone et al. |
| 6,402,750 B1 | 6/2002 | Atkinson et al. |
| 6,419,704 B1 | 7/2002 | Ferree |
| 6,436,098 B1 | 8/2002 | Michelson |
| 6,440,142 B1 | 8/2002 | Ralph et al. |
| 6,447,547 B1 | 9/2002 | Michelson |
| 6,451,019 B1 | 9/2002 | Zucherman et al. |
| 6,478,823 B1 | 11/2002 | Michelson |
| 6,488,710 B2 | 12/2002 | Besselink |
| 6,491,695 B1 | 12/2002 | Roggenbuck |
| 6,491,724 B1 | 12/2002 | Ferree |
| 6,511,484 B2 | 1/2003 | Torode et al. |
| 6,520,967 B1 | 2/2003 | Cauthen |
| 6,533,791 B1 | 3/2003 | Betz et al. |
| 6,562,072 B1 | 5/2003 | Fuss et al. |
| 6,575,978 B2 | 6/2003 | Peterson et al. |
| 6,595,995 B2 | 7/2003 | Zdeblick et al. |
| 6,599,291 B1 | 7/2003 | Foley et al. |
| 6,599,294 B2 | 7/2003 | Fuss et al. |
| 6,610,089 B1 | 8/2003 | Liu et al. |
| 6,613,089 B1 | 9/2003 | Estes et al. |
| 6,613,090 B2 | 9/2003 | Fuss et al. |
| 6,620,196 B1 | 9/2003 | Trieu |
| 6,635,060 B2 | 10/2003 | Hanson et al. |
| 6,652,533 B2 | 11/2003 | O'Neil |
| 6,666,866 B2 | 12/2003 | Martz et al. |
| 6,666,889 B1 | 12/2003 | Commarmond |
| 6,676,703 B2 | 1/2004 | Biscup |
| 6,699,288 B2 | 3/2004 | Moret |
| 6,712,819 B2 | 3/2004 | Zucherman et al. |
| 6,716,247 B2 | 4/2004 | Michelson |
| 6,719,794 B2 | 4/2004 | Gerber et al. |
| 6,733,504 B2 | 5/2004 | Lin et al. |
| 6,733,534 B2 | 5/2004 | Sherman |
| 6,743,255 B2 | 6/2004 | Ferree |
| 6,746,454 B2 | 6/2004 | Winterbottom et al. |
| 6,746,484 B1 | 6/2004 | Liu et al. |
| 6,755,837 B2 | 6/2004 | Ebner |
| 6,764,491 B2 | 7/2004 | Frey et al. |
| 6,767,366 B2 | 7/2004 | Lee et al. |
| 6,793,679 B2 | 9/2004 | Michelson |
| 6,805,695 B2 | 10/2004 | Keith et al. |
| 6,814,737 B2 | 11/2004 | Cauthen |
| 6,830,570 B1 | 12/2004 | Frey et al. |
| 6,830,574 B2 | 12/2004 | Heckele et al. |
| 6,833,006 B2 | 12/2004 | Foley et al. |
| 6,837,905 B1 | 1/2005 | Lieberman |
| 6,875,213 B2 | 4/2005 | Michelson |
| 6,893,464 B2 | 5/2005 | Kiester |
| 6,923,811 B1 | 8/2005 | Carl et al. |
| 6,923,813 B2 | 8/2005 | Phillips et al. |
| 6,929,647 B2 | 8/2005 | Cohen |
| 6,939,318 B2 | 9/2005 | Stenzel |
| 6,974,480 B2 | 12/2005 | Messerli et al. |
| 6,986,772 B2 | 1/2006 | Michelson |
| 7,063,725 B2 | 6/2006 | Foley |
| 7,087,055 B2 | 8/2006 | Lim et al. |
| 7,115,132 B2 | 10/2006 | Errico et al. |
| 7,147,641 B2 | 12/2006 | Chen |
| 7,235,081 B2 | 6/2007 | Errico et al. |
| 7,235,082 B2 | 6/2007 | Bartish et al. |
| 7,244,258 B2 | 7/2007 | Burkus et al. |
| 7,500,991 B2 | 3/2009 | Bartish et al. |
| 7,559,930 B2 * | 7/2009 | Allard et al. ............... 606/86 A |
| 7,575,580 B2 | 8/2009 | Lim et al. |
| 7,608,080 B2 | 10/2009 | Shipp et al. |
| 7,648,506 B2 * | 1/2010 | McCord et al. ............ 606/86 A |
| 7,758,647 B2 | 7/2010 | Arnin et al. |
| 2001/0034553 A1 | 10/2001 | Michelson |
| 2001/0047208 A1 | 11/2001 | Michelson |
| 2002/0013624 A1 | 1/2002 | Michelson |
| 2002/0019637 A1 | 2/2002 | Frey et al. |
| 2002/0022856 A1 | 2/2002 | Johnson et al. |
| 2002/0022886 A1 | 2/2002 | Fuss et al. |
| 2002/0026244 A1 | 2/2002 | Trieu |
| 2002/0055745 A1 | 5/2002 | McKinley et al. |
| 2002/0065558 A1 | 5/2002 | Varga et al. |
| 2002/0065560 A1 | 5/2002 | Varga et al. |
| 2002/0077700 A1 | 6/2002 | Varga et al. |
| 2002/0087212 A1 | 7/2002 | James et al. |
| 2002/0091390 A1 | 7/2002 | Michelson |
| 2002/0116006 A1 | 8/2002 | Cohen |
| 2002/0143400 A1 | 10/2002 | Biscup |
| 2002/0161443 A1 | 10/2002 | Michelson |
| 2002/0165550 A1 | 11/2002 | Frey et al. |
| 2002/0173851 A1 | 11/2002 | McKay |
| 2003/0014118 A1 | 1/2003 | Lambrecht et al. |
| 2003/0055427 A1 | 3/2003 | Graf |
| 2003/0065394 A1 | 4/2003 | Michelson |
| 2003/0074075 A1 | 4/2003 | Thomas et al. |
| 2003/0083747 A1 | 5/2003 | Winterbottom et al. |
| 2003/0093155 A1 | 5/2003 | Lambrecht et al. |
| 2003/0105527 A1 | 6/2003 | Bresina et al. |
| 2003/0125739 A1 | 7/2003 | Bagga et al. |
| 2003/0135275 A1 | 7/2003 | Garcia et al. |
| 2003/0135279 A1 | 7/2003 | Michelson |
| 2003/0139816 A1 | 7/2003 | Michelson |
| 2003/0149438 A1 | 8/2003 | Nichols et al. |
| 2003/0149482 A1 | 8/2003 | Michelson |
| 2003/0176926 A1 | 9/2003 | Boehm et al. |
| 2003/0199983 A1 | 10/2003 | Michelson |
| 2003/0208203 A1 | 11/2003 | Lim et al. |
| 2003/0229358 A1 | 12/2003 | Errico et al. |
| 2004/0002719 A1 | 1/2004 | Oz et al. |
| 2004/0030392 A1 | 2/2004 | Lambrecht et al. |
| 2004/0039392 A1 | 2/2004 | Trieu |
| 2004/0044412 A1 | 3/2004 | Lambrecht |
| 2004/0082999 A1 | 4/2004 | Mathys, Jr. et al. |
| 2004/0117020 A1 | 6/2004 | Frey et al. |
| 2004/0127990 A1 | 7/2004 | Bartish et al. |
| 2004/0133280 A1 | 7/2004 | Trieu |
| 2004/0153065 A1 | 8/2004 | Lim |
| 2004/0167538 A1 | 8/2004 | Gerber et al. |
| 2004/0193271 A1 | 9/2004 | Fraser et al. |
| 2004/0210315 A1 | 10/2004 | Li et al. |
| 2004/0225289 A1 | 11/2004 | Biedermann et al. |
| 2004/0225361 A1 | 11/2004 | Glenn et al. |

| | | |
|---|---|---|
| 2005/0027360 A1 | 2/2005 | Webb et al. |
| 2005/0033305 A1 | 2/2005 | Schultz |
| 2005/0038431 A1 | 2/2005 | Bartish et al. |
| 2005/0038513 A1 | 2/2005 | Michelson |
| 2005/0049708 A1 | 3/2005 | Atkinson et al. |
| 2005/0070900 A1 | 3/2005 | Serhan et al. |
| 2005/0080422 A1 | 4/2005 | Otte et al. |
| 2005/0090824 A1 | 4/2005 | Shluzas et al. |
| 2005/0096745 A1 | 5/2005 | Andre et al. |
| 2005/0113838 A1 | 5/2005 | Phillips et al. |
| 2005/0119747 A1 | 6/2005 | Fabris et al. |
| 2005/0131419 A1 | 6/2005 | McCord et al. |
| 2005/0131420 A1 | 6/2005 | Techiera et al. |
| 2005/0143749 A1* | 6/2005 | Zalenski et al. ............... 606/99 |
| 2005/0143822 A1 | 6/2005 | Paul |
| 2005/0143827 A1 | 6/2005 | Globerman et al. |
| 2005/0149195 A1 | 7/2005 | Boyd et al. |
| 2005/0149197 A1 | 7/2005 | Cauthen |
| 2005/0159817 A1 | 7/2005 | Ferree |
| 2005/0171554 A1 | 8/2005 | Estes et al. |
| 2005/0171609 A1 | 8/2005 | Humphreys et al. |
| 2005/0187625 A1 | 8/2005 | Wolek et al. |
| 2005/0187629 A1 | 8/2005 | Michelson |
| 2005/0261681 A9 | 11/2005 | Branch et al. |
| 2005/0278027 A1 | 12/2005 | Hyde et al. |
| 2006/0004456 A1 | 1/2006 | McKay |
| 2006/0058793 A1 | 3/2006 | Michelson |
| 2006/0100705 A1 | 5/2006 | Puno et al. |
| 2006/0129244 A1 | 6/2006 | Ensign |
| 2006/0178673 A1 | 8/2006 | Curran |
| 2006/0200164 A1 | 9/2006 | Michelson |
| 2006/0229627 A1 | 10/2006 | Hunt et al. |
| 2006/0235426 A1 | 10/2006 | Lim et al. |
| 2006/0241641 A1 | 10/2006 | Albans et al. |
| 2006/0241760 A1 | 10/2006 | Randall et al. |
| 2006/0241761 A1 | 10/2006 | Gately |
| 2007/0010826 A1 | 1/2007 | Rhoda et al. |
| 2007/0067035 A1 | 3/2007 | Falahee |
| 2007/0093904 A1 | 4/2007 | Biedermann et al. |
| 2007/0123985 A1 | 5/2007 | Errico et al. |
| 2007/0142843 A1* | 6/2007 | Dye ............................... 606/99 |
| 2007/0225726 A1 | 9/2007 | Dye et al. |
| 2007/0225808 A1 | 9/2007 | Warnick |
| 2007/0260314 A1 | 11/2007 | Biyani |
| 2007/0276406 A1 | 11/2007 | Mahoney et al. |
| 2008/0009880 A1 | 1/2008 | Warnick et al. |
| 2008/0077153 A1 | 3/2008 | Pernsteiner et al. |
| 2008/0125865 A1 | 5/2008 | Abdelgany |
| 2008/0140205 A1 | 6/2008 | Richelsoph |
| 2009/0276049 A1 | 11/2009 | Weiland |

FOREIGN PATENT DOCUMENTS

| | | |
|---|---|---|
| WO | WO 98/01091 A | 1/1998 |
| WO | WO-66045 | 11/2000 |
| WO | WO-128465 | 4/2001 |
| WO | WO-217823 | 3/2002 |
| WO | WO-2058594 | 8/2002 |

* cited by examiner

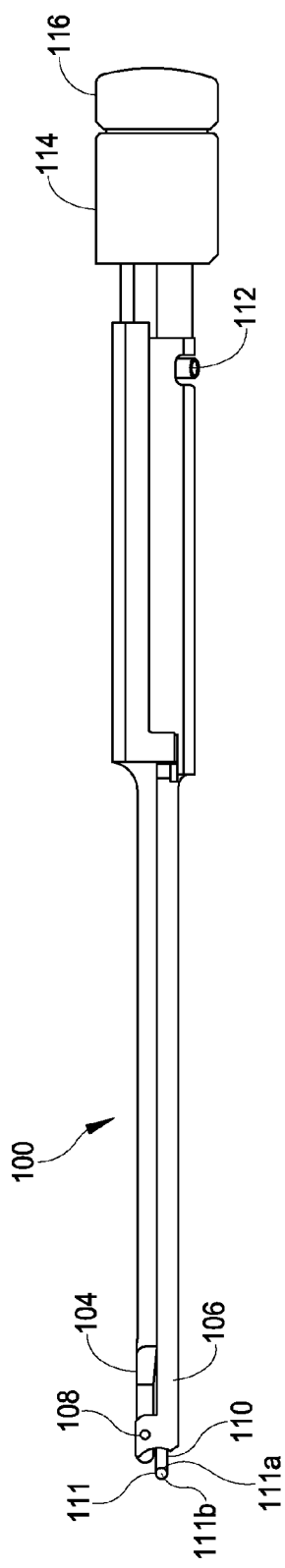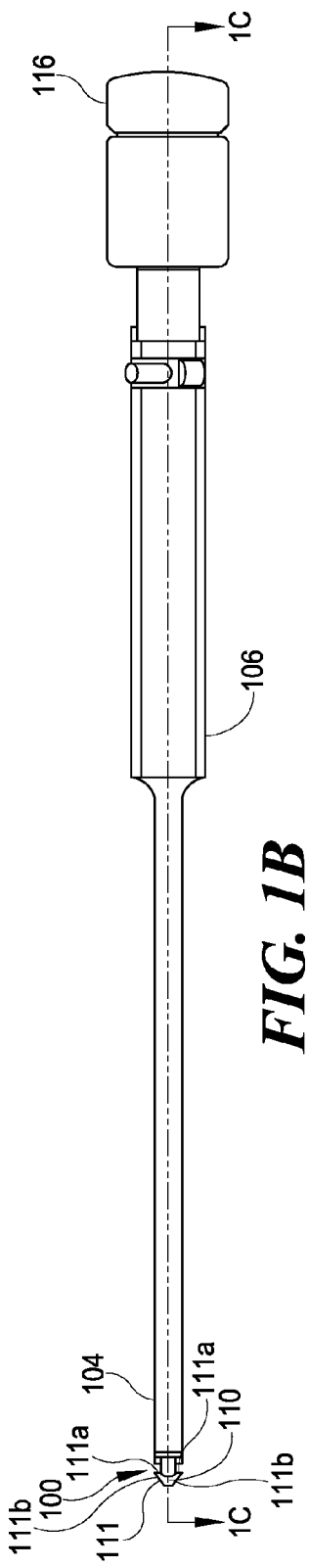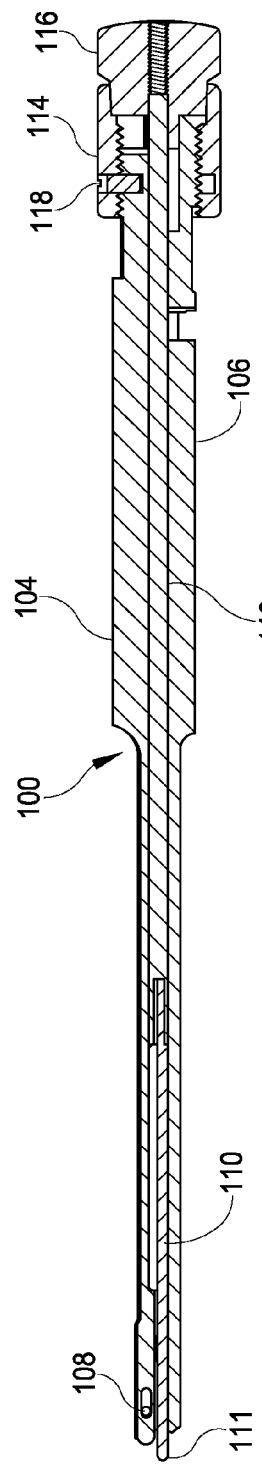

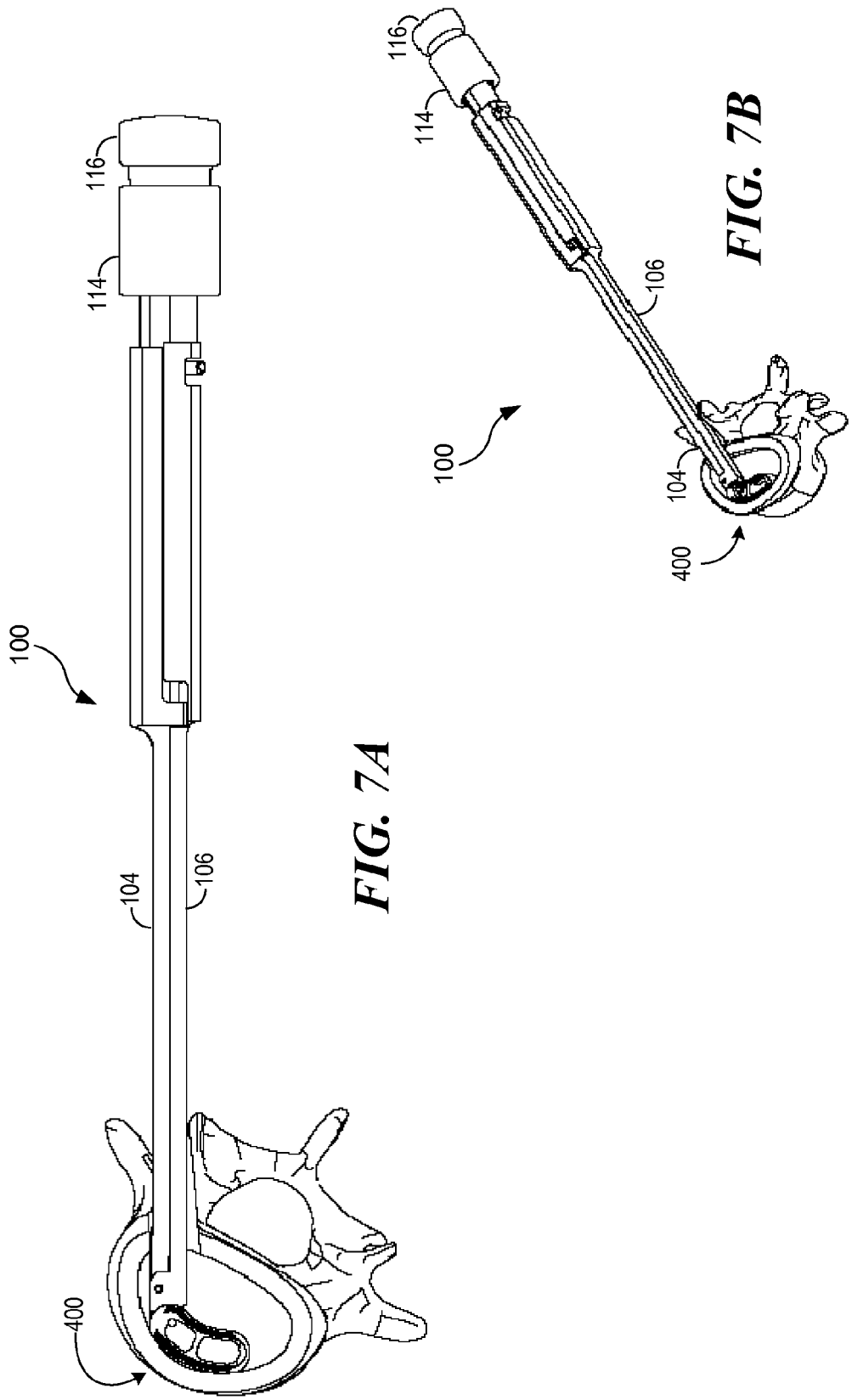

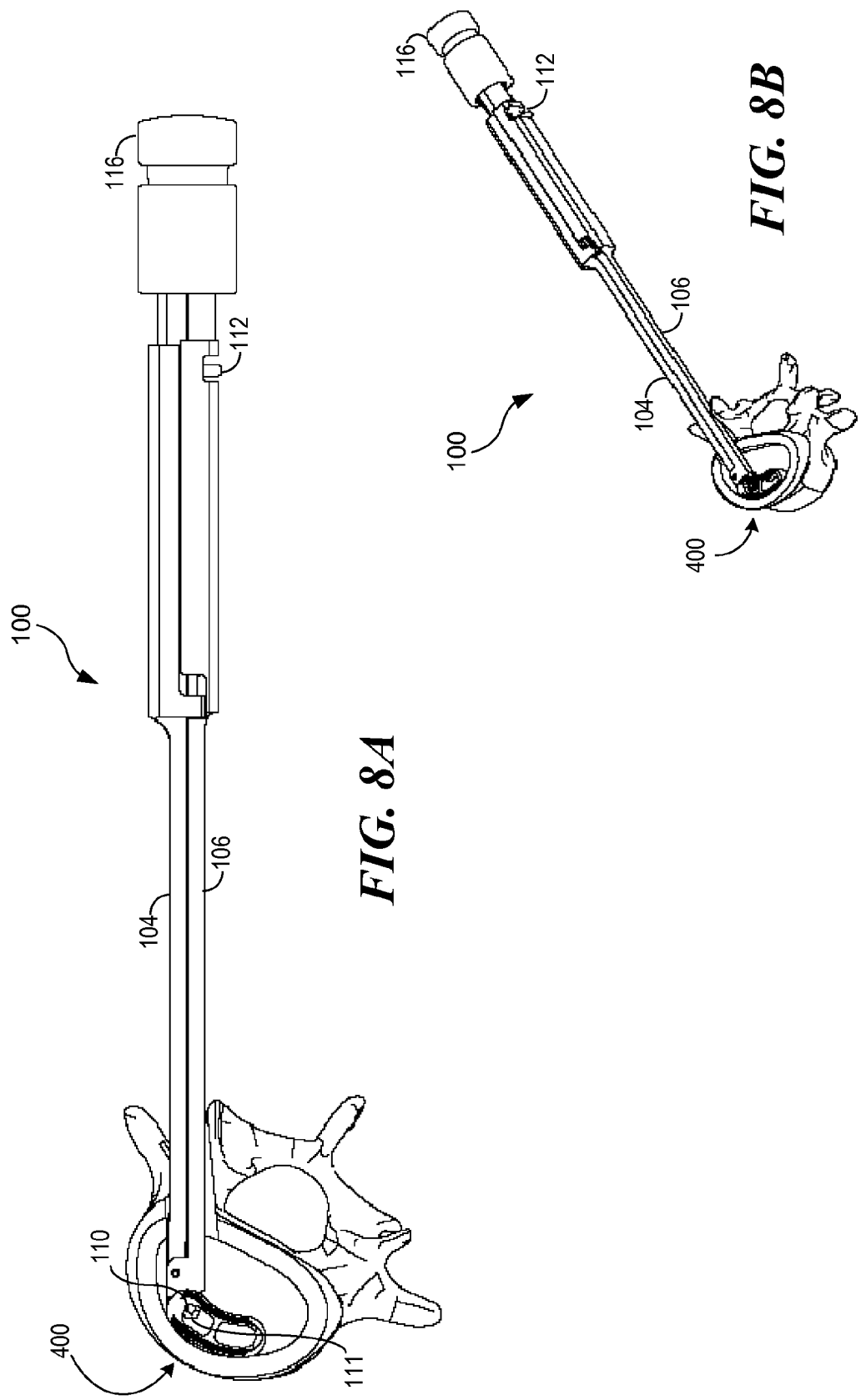

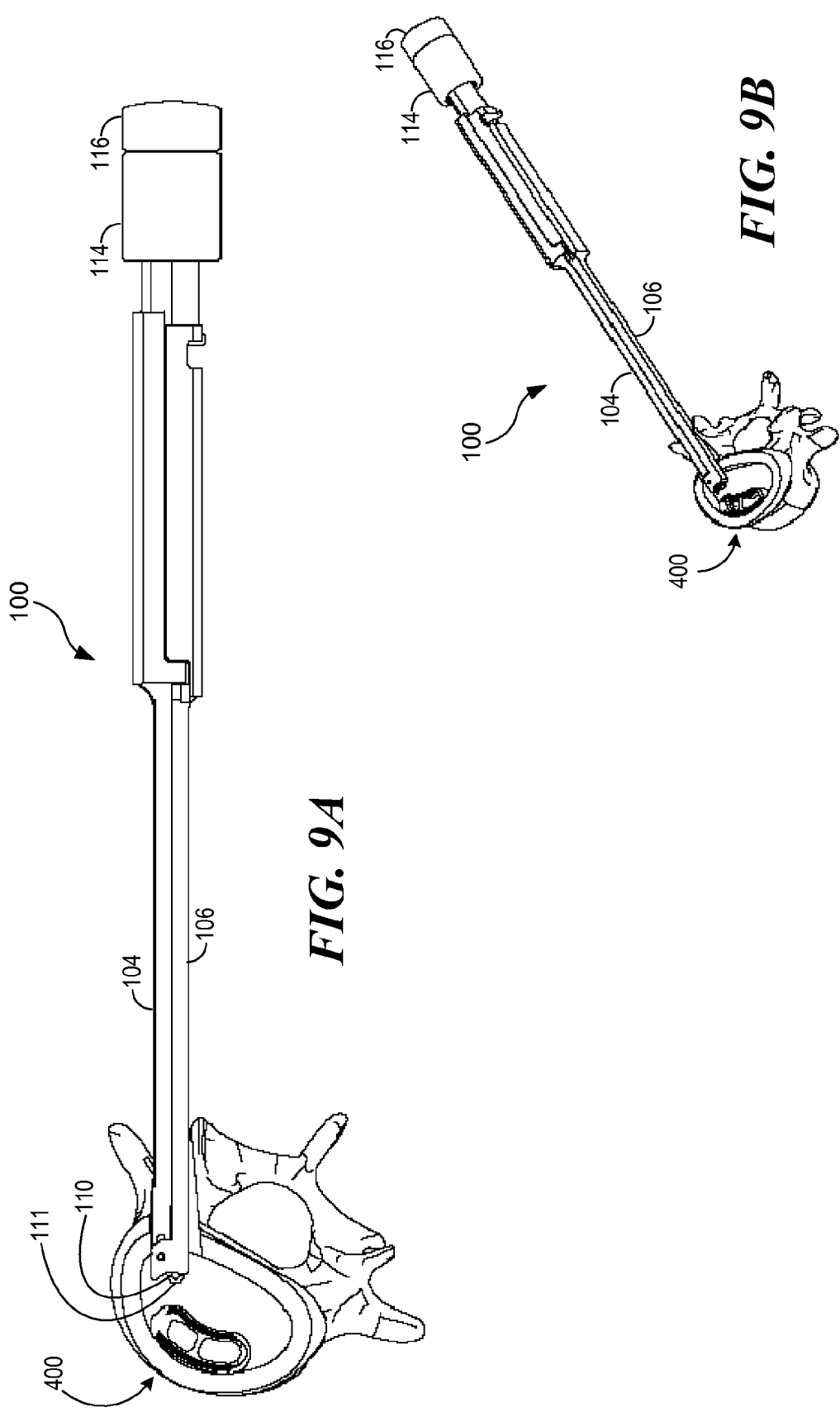

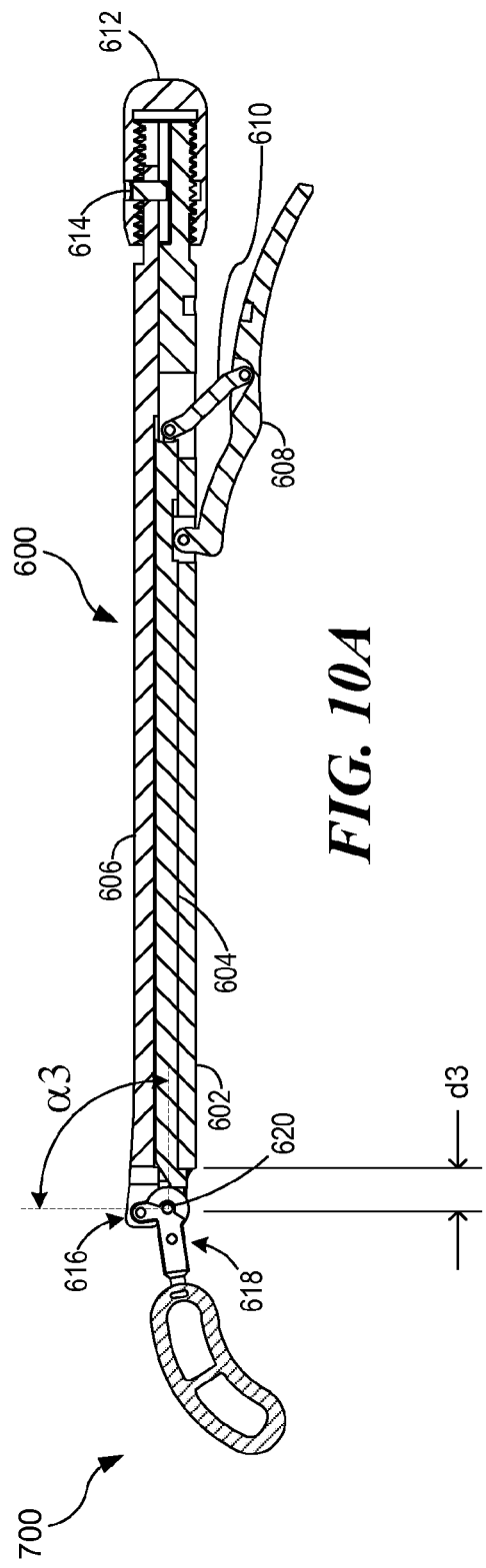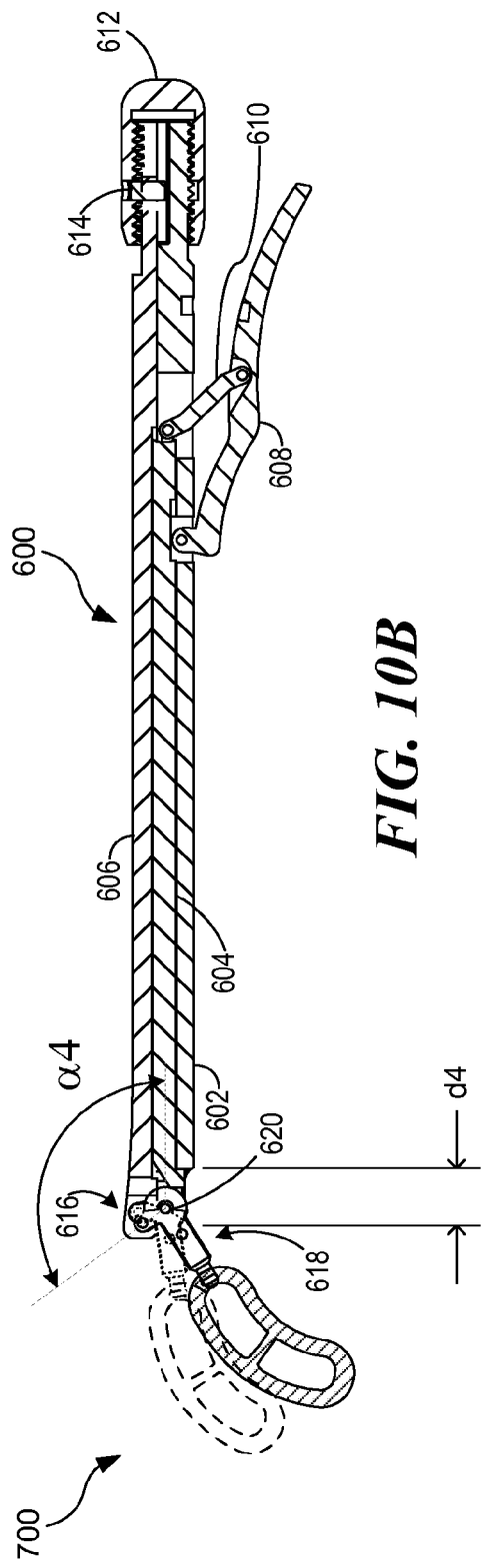

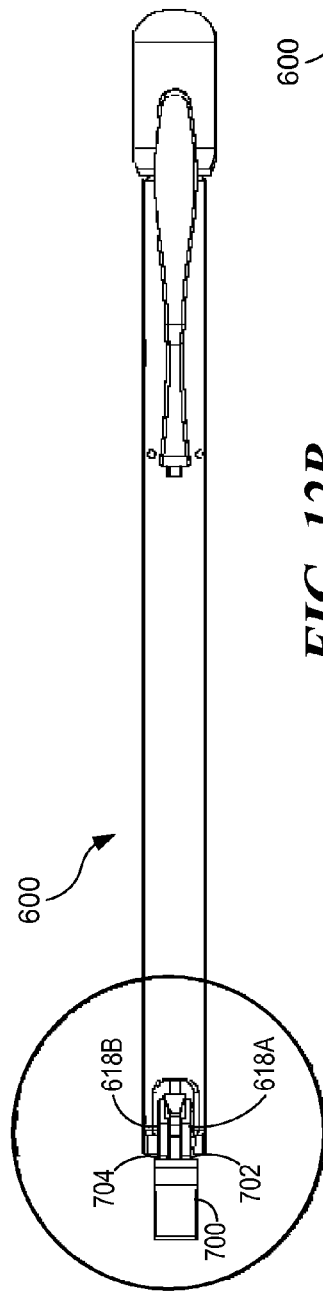
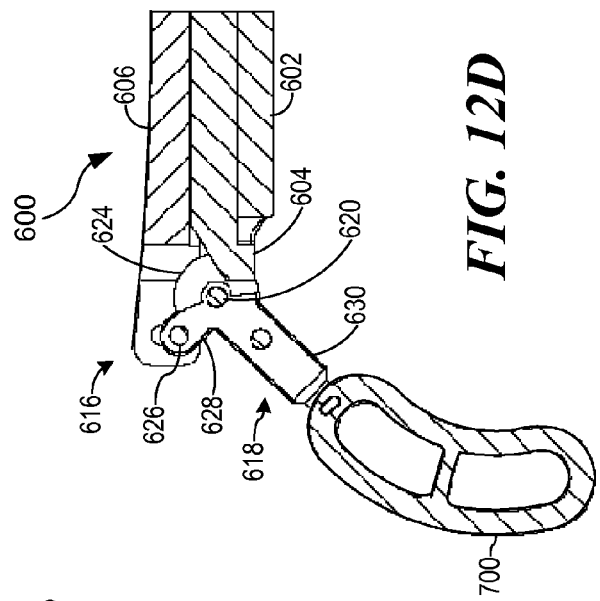
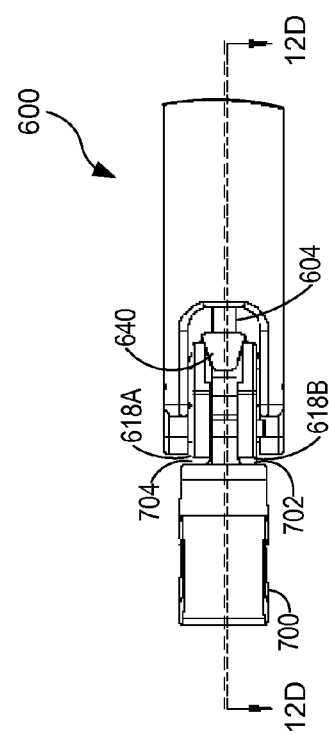
FIG. 12A
FIG. 12B
FIG. 12C
FIG. 12D

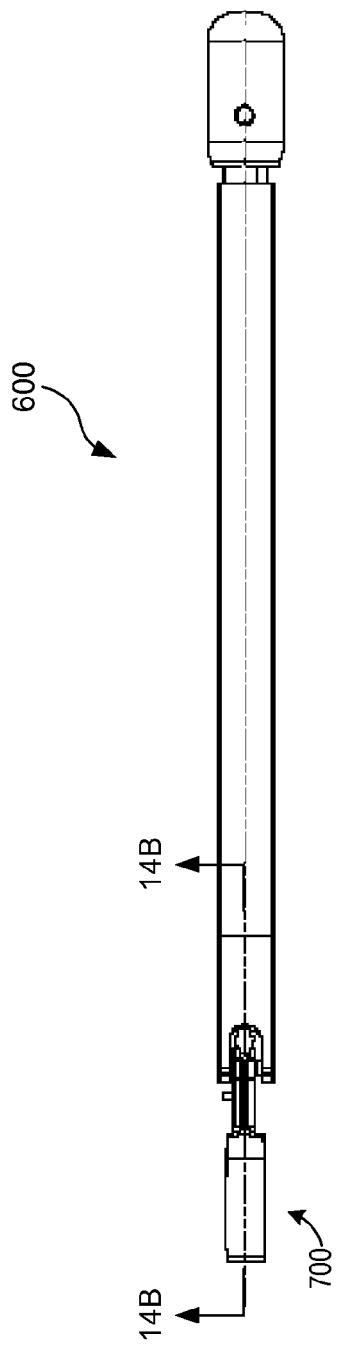
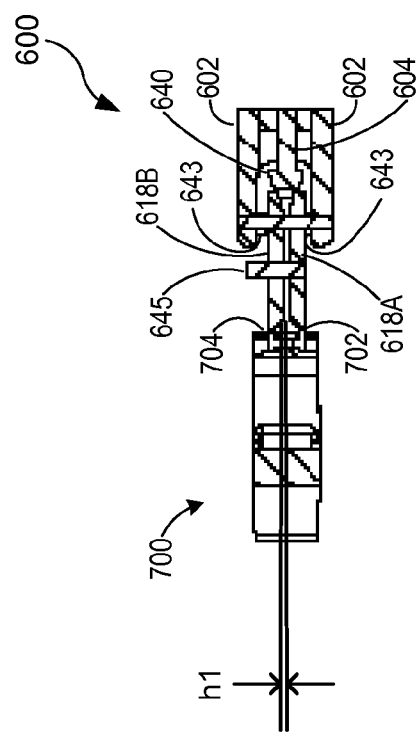
FIG. 14A
FIG. 14B

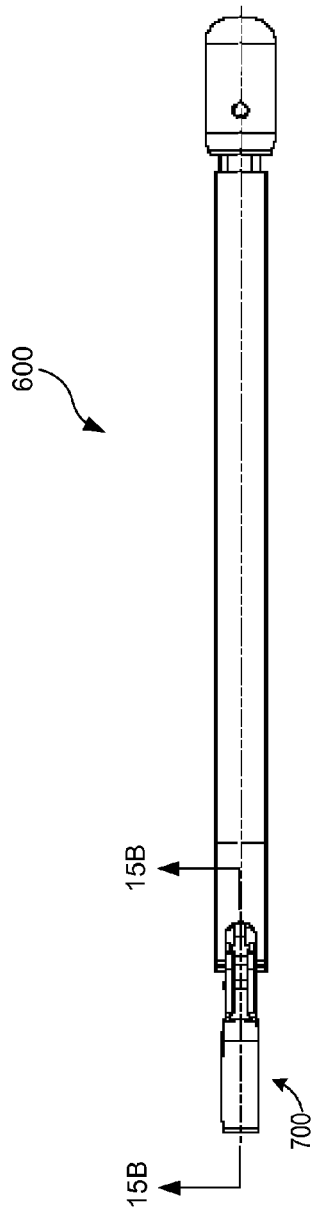
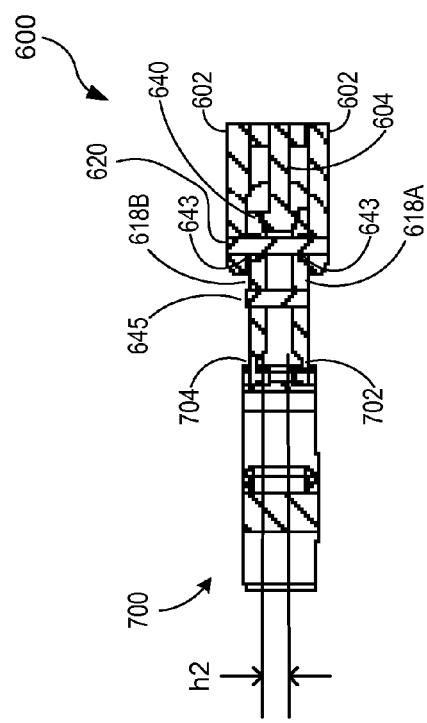

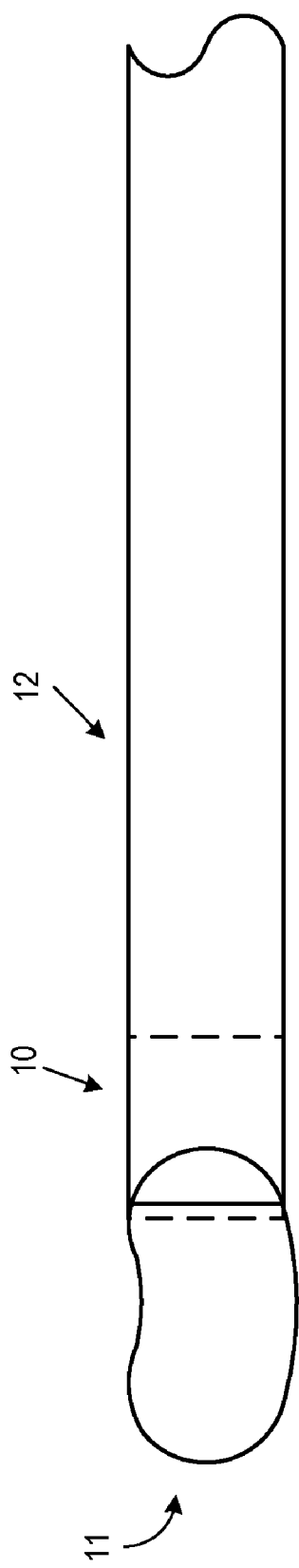

INSTRUMENTS FOR DELIVERING SPINAL IMPLANTS

CROSS-REFERENCE TO RELATED APPLICATIONS

This application claims priority from and commonly assigned U.S. Provisional Patent Application entitled "Spinal Implant Delivery Instrument" by Dye et al., filed Mar. 23, 2006, Ser. No. 60/785,318, and to U.S. Provisional Patent Application entitled "Instruments for Delivering Spinal Implants" by Justin Dye, filed Sep. 8, 2006, Ser. No. 60/825,084, which are hereby incorporated by reference as if set forth in full. This application also relates to U.S. Provisional Patent Application entitled "Articulated Delivery Instrument" by Justin Dye, filed Dec. 21, 2005, Ser. No. 60/752,544, and to U.S. patent application No. 60/825,089 entitled OFFSET RADIUS LORDOSIS, filed Sep. 8, 2006, and to U.S. patent application Ser. No. 11/614,540, entitled "Articulated Delivery Instrument" filed Dec. 21, 2006, and to U.S. patent application Ser. No. 11/690,677, entitled "FLEXIBLE CAGE SPINAL IMPLANT" filed Mar. 23, 2007, all of which are incorporated herein by reference as if set forth in full.

BACKGROUND OF THE INVENTION

Field of the Invention

This disclosure relates to systems and methods for the stabilization of human spines, and, more particularly, to instruments for inserting spinal implants for lumbar interbody fusion devices.

The human spine is a complex structure designed to achieve a myriad of tasks, many of them of a complex kinematic nature. The spinal vertebrae allow the spine to flex in three axes of movement relative to the portion of the spine in motion. These axes include the horizontal (i.e., bending either forward/anterior or aft/posterior), roll (i.e., lateral bending to either left or right side), and rotation (i.e., twisting of the shoulders relative to the pelvis).

The intervertebral spacing (e.g., between neighboring vertebrae) in a healthy spine is maintained by a compressible and somewhat elastic disc. The disc serves to enable the spine to move about the various axes of rotation and through the various arcs and movements required for normal mobility. The elasticity of the disc maintains the spacing between the vertebrae during flexion and lateral bending of the spine, allowing room or clearance for compression of neighboring vertebrae. In addition, the disc enables relative rotation about the vertical axis of neighboring vertebrae, allowing for the twisting of the shoulders relative to the hips and pelvis. The clearance between neighboring vertebrae, as maintained by a healthy disc, is also important to allow the nerves from the spinal cord to extend out from the spine, e.g., between neighboring vertebrae, without being squeezed or impinged by the adjacent vertebrae.

In situations (e.g., based upon injury or otherwise) where a disc is not functioning properly, the inter-vertebral disc tends to compress, and in doing so pressure is exerted on nerves extending from the spinal cord by the reduced inter-vertebral spacing. Various other types of nerve problems may be experienced in the spine, such as exiting nerve root compression in neural foramen, passing nerve root compression, and enervated annulus (i.e., where nerves grow into a cracked/compromised annulus, causing pain every time the disc/annulus is compressed), as examples. Many medical procedures have been devised to alleviate such nerve compression and the pain that results from the nerve pressure. Many of these procedures revolve around attempts to prevent the vertebrae from moving too close to each other by surgically removing an improperly functioning disc and replacing it with a lumbar interbody fusion device or spacer. Although prior interbody devices, including spacers, may be effective at improving the condition of a patient, the vertebrae of the spine, body organs, the spinal cord, other nerves, and other adjacent bodily structures make it difficult to obtain surgical access to the locations between the vertebrae where the spacer is to be installed.

Generally speaking, using a less invasive surgical technique for a spinal surgical procedure will minimize trauma to the surrounding bone, tissues, and muscle, and improve the condition of a patient after surgery. What is needed, therefore, are instruments for the delivery of interbody devices in a minimally invasive manner.

SUMMARY

An embodiment of the present invention may comprise a medical instrument for placing an insert in a space between boney structures in vivo. The instrument may comprise a body, an articulating member slidably coupled to the body and adapted to engage an attached insert, and an articulator operatively coupled to the articulating member. Actuating the articulator may translate the articulating member with respect to the body. In addition, the instrument may comprise an engagement member coupled to the body and may be configured to releasably and rotatably secure the insert to the instrument. The articulating member and the engagement member may be offset in a transverse direction such that when the articulating member engages the attached insert, the insert will rotate relative to the instrument.

An embodiment of the present invention may comprise a method for inserting an insert into a space between boney structures using a medical instrument. The method may comprise coupling the insert to a distal end of the instrument, inserting the insert to a position proximate to the space between the boney structures, and impacting a proximal end of the instrument to drive the insert into the space. The method may further comprise actuating an articulator to translate an articulating member, thereby rotating the insert relative to the instrument. Additionally, the method may comprise releasing the insert from the instrument and withdrawing the instrument from the space between the boney structures.

BRIEF DESCRIPTION OF THE DRAWINGS

For a more complete understanding of this disclosure, reference is now made to the following Detailed Description taken in conjunction with the accompanying drawings, in which:

FIG. 1A illustrates a sagittal view of an embodiment of a delivery instrument designed to insert a spacer into the intervertebral space;

FIG. 1B illustrates a bottom view of the delivery instrument of FIG. 1A;

FIG. 1C illustrates a cross-sectional view of the delivery instrument of FIG. 1B taken along the line 1C-1C;

FIG. 7A illustrates a sagittal view of the instrument of FIG. 1 and the spacer of FIG. 4, detailing the proper placement of the spacer in the intervertebral space;

FIG. 7B illustrates an oblique view of the instrument of FIG. 1 and the spacer of FIG. 4, detailing the proper placement of the spacer in the intervertebral space;

FIG. 8A illustrates a sagittal view of the instrument of FIG. 1 and the spacer of FIG. 4, detailing the release of the spacer in the intervertebral space;

FIG. 8B illustrates an oblique view of the instrument of FIG. 1 and the spacer of FIG. 4, detailing the release of the spacer in the intervertebral space;

FIG. 9A illustrates a sagittal view of the instrument of FIG. 1 and the spacer of FIG. 4, detailing the removal of the instrument from the intervertebral space;

FIG. 9B illustrates an oblique view of the instrument of FIG. 1 and the spacer of FIG. 4, detailing the removal of the instrument from the intervertebral space.

FIG. 10A illustrates a cross-sectional view of an alternative embodiment of a delivery instrument designed to insert a spacer into the intervertebral space;

FIG. 10B illustrates a cross-sectional view of the delivery instrument of FIG. 10A with the spacer slightly rotated relative to the delivery instrument;

FIG. 12A illustrates a side view of the delivery instrument of FIG. 10A with the spacer attached;

FIG. 12B illustrates a bottom view of the delivery instrument of FIG. 12A with the spacer attached;

FIG. 12C illustrates an enlarged detailed bottom view of a distal end of the delivery instrument of FIG. 12B with the spacer attached;

FIG. 12D illustrates an enlarged detailed cross-sectional side view of the distal end of the delivery instrument with the spacer attached;

FIG. 14A illustrates a top view of the delivery instrument of FIG. 10A with the spacer engaged by a holder;

FIG. 14B illustrates an enlarged detailed cross-section view of the delivery instrument of FIG. 14A with the spacer engaged by the holder, as taken along the line 14B-14B;

FIG. 15A illustrates a top view of the delivery instrument of FIG. 10A with the spacer released by a holder;

FIG. 15B illustrates a detailed cross-section view of the delivery instrument of FIG. 15A with the spacer released by the holder, as taken along the line 15B-15B;

FIG. 20 illustrates a side elevation view of a delivery instrument constructed in accordance with another embodiment of the present invention.

DETAILED DESCRIPTION

Figure 2:
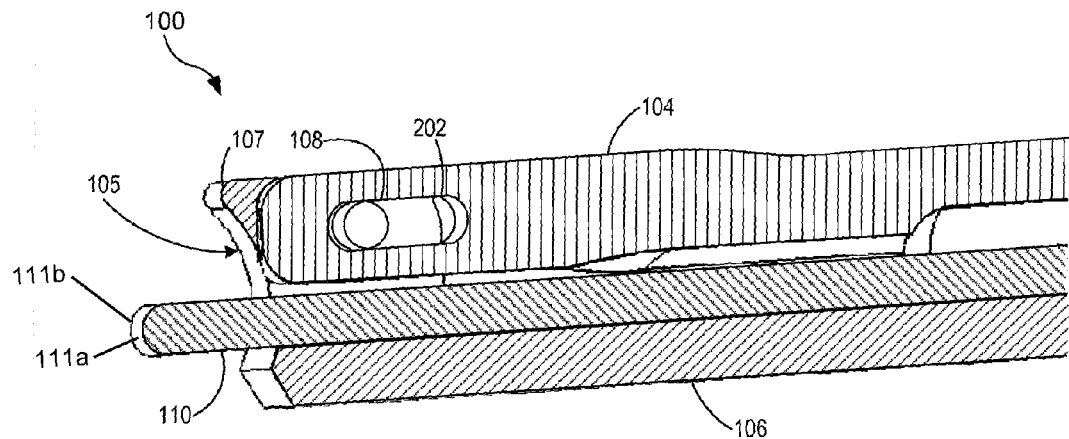
FIG. 2 illustrates an enlarged cross-sectional view of a distal end of the delivery instrument of FIG. 1A.

In the following discussion, numerous specific details are set forth to provide a thorough understanding of the present invention. However, those skilled in the art will appreciate that the present invention may be practiced without such specific details. In other instances, well-known elements may have been illustrated in schematic or block diagram form in order not to obscure the present invention in unnecessary detail. Additionally, for the most part, details concerning well known features and elements may have been omitted inasmuch as such details are not considered necessary to obtain a complete understanding of the present invention, and are considered to be within the understanding of persons of ordinary skill in the relevant art.

An Illustrative Embodiment

Turning now to the drawings, FIG. 1A shows a sagittal view of an illustrative embodiment of a delivery instrument 100 configured according to at least a portion of the subject matter of the present invention. The delivery instrument 100 may insert a spacer (not shown in FIG. 1A) into an intervertebral space and properly position the spacer therein. After which, the delivery instrument 100 may then release the spacer from the delivery instrument 100 or withdraw the spacer without ever releasing it. FIG. 1B illustrates a bottom view of the delivery instrument 100. FIG. 1C shows a cross-sectional view of the delivery instrument 100 of FIG. 1A.

As seen in FIG. 1A, the delivery instrument 100 may comprise an articulating member 104 translatably coupled to a main body 106. One or more pins, for example, may be used to couple the articulating member 104 to the main body 106. In one embodiment, one pin 108 may couple the articulating member 104 to the main body 106 at a distal end of the delivery instrument 100. Accordingly, the pin 108 may allow the translating sliding movement of the articulating member 104 with respect to the main body 106, while still coupling together the articulating member 104 and the main body 106. In certain embodiments, the delivery instrument may further comprise an engagement member 110 used to attach a spacer to the delivery instrument 100. The engagement member 110 may comprise a connecting member 111 located at a distal end of the engagement member 110.

An articulation knob or rotating member 114 may be operatively coupled to the articulating member 104 and the main body 106, such that, operation of the articulation knob 114 may translate the articulating member 104 with respect to the main body 106. In certain embodiments, the instrument 100 may further comprise an engagement knob 116, operatively coupled to the engagement member 110. Rotation of the engagement knob 116 may loosen or tighten a securing force established between the engagement member 110 and an attached spacer (not shown in FIG. 1A). An engagement lever or release member 112 may be coupled to the engagement member 110 at an intermediate section of the delivery instrument 100 so as to allow a user to rotate the engagement member 110 through approximately 90 degrees about a longitudinal axis of the engagement member 110.

Turning now to FIG. 1B, the engagement member 110 may comprise a connecting member or cross-member 111 at a distal end (for example, a substantially T-shaped member, a spherical member, an angular member, among other configurations). Cross-member 111 may include one or more arms 111a, each with a slanted portion 111b. Of course, the engagement member 110 may be configured differently and still be able to secure the spacer (not shown in FIG. 1B) to the main body 106. For instance, as two examples from amongst many additional embodiments, the connecting member 111 of the engagement member 110 may form an "L" shape, or arms comprising the connecting member 111 may have non-cylindrical cross-sections. A longitudinal portion of the engagement member 110, which may extend along the length of the delivery instrument 100, may be slender enough to allow the flexing of the longitudinal portion during the movement of an attached articulating spacer. The flexing of the engagement member 110 may facilitate the rotating movement or articulation of the attached spacer. In addition, in some embodiments the flexing of the engagement member 110 may facilitate engagement of the connecting member 111 with an internal engagement recess or recess 402 (see FIGS. 4A and 4C) of an attached spacer (described later). The attached spacer may be articulated due to an interaction between the spacer and the articulating member 104. In addition, a user may loosen the engagement knob 116 prior to articulating the spacer in order to allow the engagement member 110 to slightly translate as the spacer slidably cams against the end portion of the body 106 (i.e., the loosening of the engagement knob 116 may provide a slight increase in the distance between the connecting member 111 and the end of the body 106). The attachment of the connecting member 111 to the spacer will be described in detail later with reference to FIGS. 5A and 5B. As more clearly shown in FIGS. 1A and 1C, the engagement member 110 may be positioned between the articulating member 104 and the body 106.

Turning now to FIG. 1C, the articulating member 104, the body 106, and the engagement member 110 may fit within the articulation knob 114 at a proximal end of the delivery instrument 100. In some embodiments, the articulation knob 114 may comprise internal threads to threadably engage with a corresponding threaded portion of the body 106. As the articulation knob 114 is rotated, the articulation knob 114 may move in either direction along and relative to the body 106. The articulating member 104 may be slidably coupled to the articulating knob 114 via a pin 118. The pin 118 may allow the articulating member 104 to move along with the articulation knob 114, and may fix the relative distance between the articulation knob 114 and the articulating member 104 in a longitudinal direction. Even though the relative distance may be fixed in the longitudinal direction, the articulation knob 114 may rotate relative to the articulating member 104. Consequently, the articulating member 104 and the articulation knob 114 may be able to move in either direction (i.e., towards the distal end and towards the proximal end of the delivery instrument 100) along and relative to the body 106. The engagement member 110 may be substantially fixed in a longitudinal direction relative to the main body 106 while the articulating member 104 and the articulation knob 114 move along and relative to the body 106. However, the engagement member 110 may still be rotated independent of the position of the articulating member 104 and the articulation knob 114.

In certain embodiments, an engagement knob 116 may be used to apply a securing force to an attached spacer (not shown in FIG. 1C) via the connecting member 111. Accordingly, the engagement member 110 may have threads at a proximal end (i.e., opposite to the connecting member 111) threadably engaged with the internal threads of the engagement knob 116. As the engagement knob 116 is rotated towards the articulation knob 114 (e.g., with a spacer attached to the delivery instrument 100) the spacer may be drawn tighter against the delivery instrument 100 to seat against a distal end of the body 106. In some embodiments, rotating the engagement knob 116 may proximally move the connecting member 111 so as to capture the spacer between the distal end of the body 106 and connecting member 111. The connecting member 111 and the distal end of the body 106 may apply a clamping force to an attached spacer located there between. In some embodiments, the distal end of the body 106 may be textured in order to apply a greater frictional force to an abutting surface of the spacer. Consequently, the engagement member 110 and the spacer may be substantially locked into place due to a force applied to an end of the engagement member 110 that pulls the engagement member 110 towards the proximal end of the delivery instrument 100.

As the engagement knob 116 becomes firmly seated against the proximal end of the body 106, the engagement member 110, engagement knob 116, main body 106, and spacer, all form a relatively rigid structure. The rigid structure may efficiently transfer a striking force upon the engagement knob 116, through the delivery instrument 100, to the spacer. This feature may allow an impact force to the main body 106 or the engagement knob 116 to be applied to the spacer, while the delivery instrument 100 remains securely attached to the spacer. By impacting the end of the delivery instrument 100, a surgeon may forcibly insert the spacer into a proper position between the boney structures. However, other embodiments may also provide this feature of the disclosure, such as a resilient member, latch mechanism, or other systems that may firmly hold together the engagement member 110 and the spacer. Additionally, other embodiments may comprise an impact head (described later) coupled to a proximal end of the delivery instrument 100 in order to more efficiently and effectively transfer force to a spacer.

When the spacer is in the proper position, the engagement knob 116 may be rotated in an opposite direction (i.e., counter clockwise relative to viewing the engagement knob from a proximal position) to disengage the connecting member 111 of the engagement member 110 from the spacer. Rotating the engagement knob 116 in the opposite direction may move the connecting member 111 distally so that the spacer is no longer secured or clamped between the connecting member 111 and the distal end of the body 106. After the engagement knob 116 is loosened, the engagement lever 112 (and correspondingly the engagement member 110) may be rotated through an angle of approximately 90 degrees. The connecting member 111 of the engagement member 110 may be rotated relative to the spacer and consequently released from the spacer. In some embodiments, the engagement knob 116 may not need to be loosened in order for the engagement member 110 to be released from the spacer. Releasing the engagement member 110 may be accomplished while the spacer remains in a substantially static position. Therefore, releasing the connecting member 111 may enable the delivery instrument 100 to be removed from an intervertebral space without significantly altering the placement position of the inserted spacer.

Referring now to FIG. 2, this figure shows an enlarged cross-sectional view of the distal end of the delivery instrument 100. The engagement member 110 may be positioned between the articulating member 104 and the body 106. The articulating member 104 may comprise an elongated opening 202. The pin 108 may move forward and backward relative to the interior of the elongated opening 202. The size and geometry of the elongated opening 202 and may define a relative range of articulating motion for an attached spacer (not shown in FIG. 2). Adjusting the size and geometry of the elongated opening 202 may alter or adjust a relative range of motion for an attached spacer. In some embodiments, the pin 108 may be fixed relative to the body 106. However, in some embodiments, the pin 108 may be attached to the articulating member 104 and the elongated opening 202 may be in the body 106. The articulating member 104 may slidingly translate back and forth (i.e., along a longitudinal direction of the delivery instrument 100) relative to the pin 108. As a result, the elongated opening 202 may enable the articulating member 104 to slidably move relative to the main body 106 without becoming uncoupled from the body 106. As the elongated member 104 moves in a distal direction towards the spacer, a front end of the pusher 104 (e.g., an abutment surface 107) may abut the spacer. The contact force between the abutment surface 107 of the articulating member 104 and the spacer may cause the spacer to rotate relative to the delivery instrument 100. As the spacer rotates, the connecting member 111 of the engagement member 110 may rotatably and slidably secure the spacer against a seating surface 105 provided at the distal end of the body 106.

Figure 3:
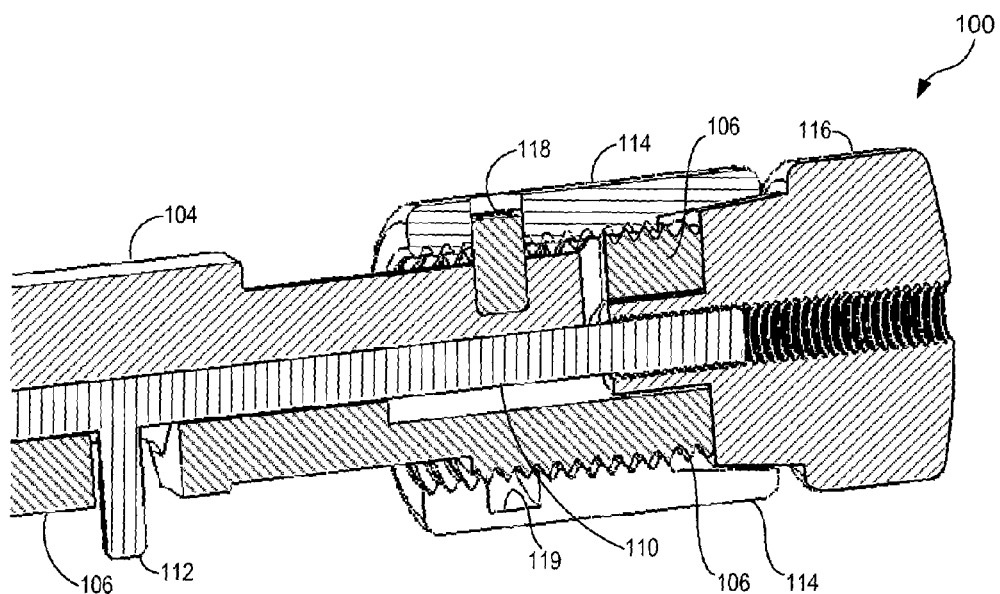
FIG. 3 illustrates an enlarged cross-sectional view of a proximal end of the delivery instrument of FIG. 1A.

Turning now to FIG. 3, this figure illustrates an enlarged cross-sectional view of the proximal end of the delivery instrument 100. The proximal end may be opposite to the end of the delivery instrument 100 that attaches to the spacer (not shown in FIG. 3). As shown in this illustrative embodiment, the articulating member 104, the body 106, and the engagement member 110 may have portions that fit inside of the articulation knob 114. In an embodiment of the present invention, the articulation knob 114 may comprise internal threads in order to threadably engage with a correspondingly threaded portion of the body 106. The articulation knob 114 may comprise a groove 119 or cut-out on the inside of the articulation knob 114 to slidably accommodate a pin 118. The engagement between the pin 118 and the groove 119 may fix the articulating member 104 and the articulation knob 114 relative to a longitudinal direction. As a result, if a user rotates the articulation knob 114, the articulating member 104 may translate along the delivery instrument 100 in sync with the translation of the articulation knob 114 along the delivery instrument 100. The translation of the articulating member 104 may thereby articulate the spacer.

The engagement knob 116 may be used to maintain the engagement member 110 in a substantially static position relative to the body 106 as well as to provide a securing force to an attached spacer (not shown in FIG. 3). The engagement member 110 may be threaded at a proximal end, opposite to the connecting member 111, and threadably engaged with the corresponding internal threads of the engagement knob 116. As the engagement knob 116 is rotated towards the articulation knob 114 (i.e., in a clockwise direction when viewed from a proximate perspective), the engagement member 110 may be moved in a proximal direction relative to the main body 106 and become securely fixed to an attached spacer due to the force applied to the engagement member 110 by the engagement knob 116. When loosening or releasing the engagement member 110, the engagement knob 116 may be rotated in a direction away from the articulation knob 114 and body 106 (i.e., in a counter clockwise direction when viewed from a proximate perspective). After loosening the engagement member 110, the engagement lever 112 may be rotated, correspondingly rotating the connecting member 111 and disengaging the engagement member 110 from an attached spacer.

Figure 4A:
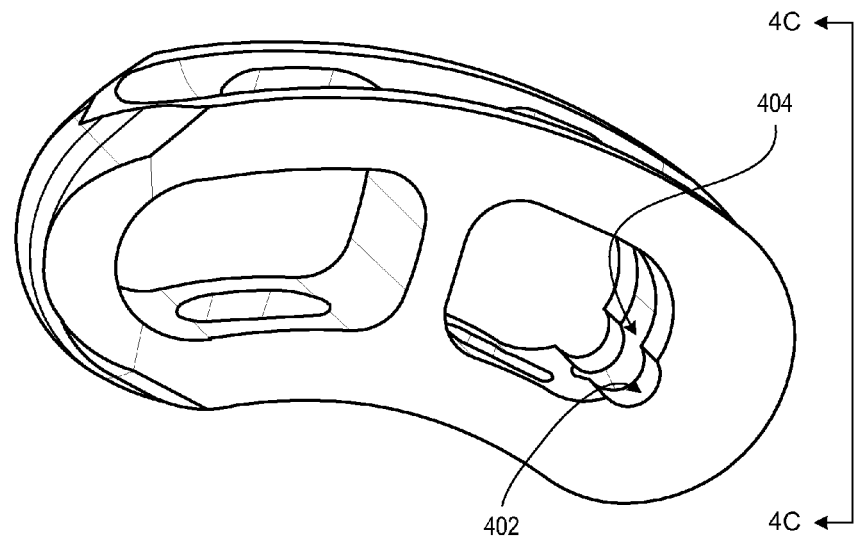
FIG. 4A illustrates an oblique view of a spacer designed to be inserted into the intervertebral space.
Figure 4B:
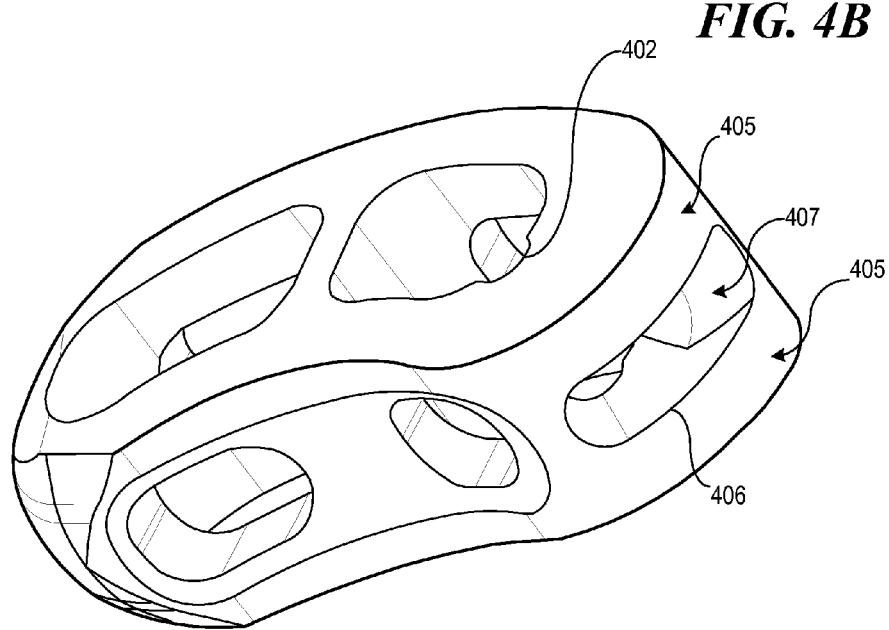
FIG. 4B illustrates a further oblique view of the spacer of FIG. 4A.
Figure 4C:
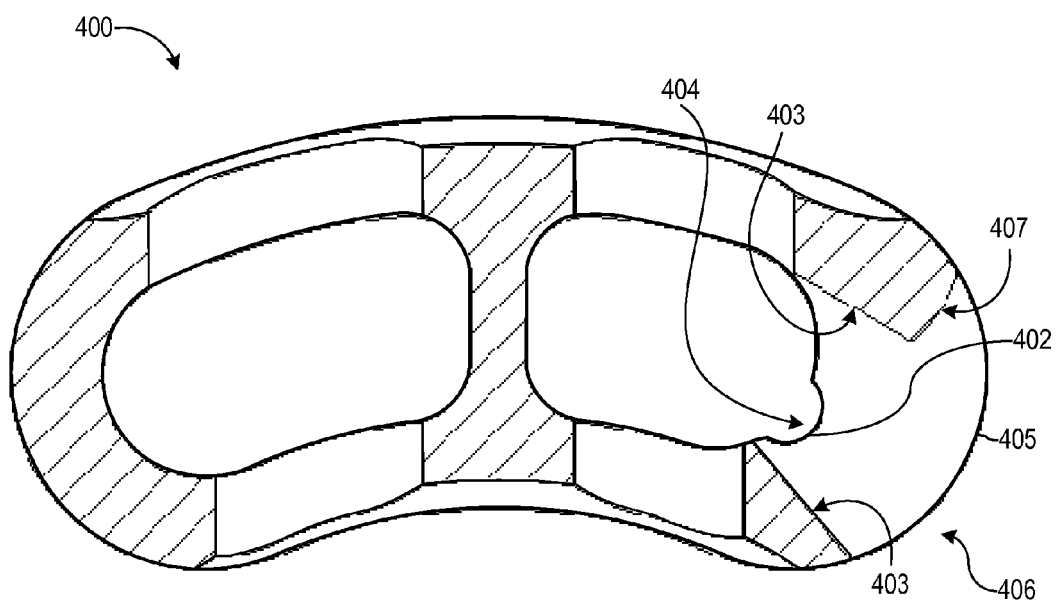
FIG. 4C illustrates a cross-sectional view of the spacer of FIG. 4A taken along the line 4C-4C.

Referring now to FIGS. 4A, 4B, and 4C, these figures respectively show upper and lower oblique views and a cross-sectional view of a spacer 400 designed to be inserted into an intervertebral space. The spacer 400 may be configured to have an engagement recess 402 and an insertion port 404. As seen in FIG. 4B, the insert 400 may further comprise a seating surface 405 on either side of an elongated opening 406, and an abutment surface 407 on an outer surface of the spacer 400. The connecting member 111 (FIG. 2) of the engagement member 110 (FIG. 1A) may be inserted through the insertion port 404 via the elongated opening 406. In certain embodiments, the connecting member 111 of the engagement member 110 may be inserted into an interior of the spacer 400 when the arms of the connecting member 111 (FIG. 1B) are substantially parallel to the side walls of the insertion port 404 and elongated opening 406 (i.e., when a central axis defining the arms of the connecting member 111 is substantially parallel to the side walls of the insertion port 404 and the elongated opening 406).

Once the arms of the connecting member 111 (FIG. 2) are inserted into the spacer 400, the engagement member 110 (FIG. 3) may be rotated through approximately 90 degrees through the operation of the engagement lever 112 (FIG. 3). As a result, the arms of the connecting member 111 may be substantially perpendicular to the side walls of the insertion port 404 and elongated opening 406. In this position, the arms of the connecting member 111 may be substantially parallel to an axis defining the engagement recess 402. The engagement member 110 may then be pulled towards the proximate end of the delivery instrument 100 (FIG. 1A) via the engagement knob 116 (FIG. 3) such that the arms of the connecting member 111 rotatably engage the engagement recess 402. The seating surface 405 of the insert 400 may slidably engage the seating surfaces 105 (FIG. 3) of the main body 106. At this point, the spacer 400 may be securely and rotatably held by the delivery instrument 100. The engagement knob 116 may be rotated to firmly secure the spacer 400 to the delivery instrument 100. In some embodiments, rotating the engagement knob 116 may apply a clamping force from the connecting member 111 and the seating surfaces 105s of the main body 106 to the spacer 400 there between. Further, although the engagement recess 402 is shown substantially orthogonal to the insertion port 404, an embodiment of the present invention may not be limited to this configuration. In certain embodiments the engagement recess 402 may be parallel to the insertion port 404, so that the engagement member 110 does not have to be rotated to secure and release a spacer 400. In such a case, the flexibility of the engagement member 110 may facilitate the engagement and release of the connecting member 111. In other embodiments, the engagement recess 402 may be at any angle to the insertion port 404, as long as the spacer 400 may be rotatably secured to the connecting member 111. Additionally, the insertion port 404 may be at any angle relative to spacer 400.

When the spacer 400 is in the proper position in the intervertebral space, the engagement knob 116 (FIG. 3) may be used to loosen the spacer 400 from the engagement member 110 (FIG. 3) by reducing the force applied to the spacer 400 via the arms of the connecting member 111 (FIG. 2) of the engagement member 110. In certain embodiments, the engagement knob 116 may be rotated in order to lower the force applied to the spacer 400 by the engagement member 110, for example, by moving the engagement member 110 distally. The flexibility of the engagement member 110 may facilitate in releasing the connecting member 111 from the engagement recess 402 of the spacer 400. The flexibility of the engagement member 110 may also aid in releasing the connecting member 110 from the spacer 400. Once the force applied to the engagement member 110 via the engagement knob 116 is reduced, the arms of the connecting member 111 may be disengaged from the engagement recess 402. The engagement member 110 may then be rotated through approximately 90 degrees relative to the spacer 400 via the engagement lever 112 (FIG. 3) so that the arms of the connecting member 111 may be substantially parallel to the side walls of the insertion port 404 and elongated opening 406. The engagement member 110 may then be removed from the spacer 400 through the insertion port 404. Releasing the spacer 400 through this method may allow the spacer 400 to remain in a substantially static position and orientation within the intervertebral space. In addition, the method may enable the delivery instrument 100 to be removed from the intervertebral space.

As more clearly seen in FIG. 4C, the seating or end surface 405 may be substantially arcuate. The abutment surface 407 may be provided inside of the seating surface 405 and connected with at least one of the side walls 403. The side walls 403 of the insertion port 404 and the elongated opening 406 may diverge toward an anterior end of the spacer 400. The diverging side walls 403 may facilitate the insertion and removal of the arms of the connecting member 111 (FIG. 2) of the engagement member 110 (FIG. 2) via the insertion port 404 and elongated opening 406. The spacer 400 may be secured to the delivery instrument 100 (FIG. 1A) as a result of the connecting member 111, provided at the distal end of the engagement member 110, attaching to the engagement recess 402 inside of the spacer 400. The engagement member 110 may be removed from the spacer 400 via the insertion port 404. The diverging side walls 403 of the insertion port 404 and the elongated opening 406 may enable the delivery instrument 100 to be removed from the spacer 400 and the intervertebral space without significantly altering the position and orientation of the spacer 400.

Figure 5A:
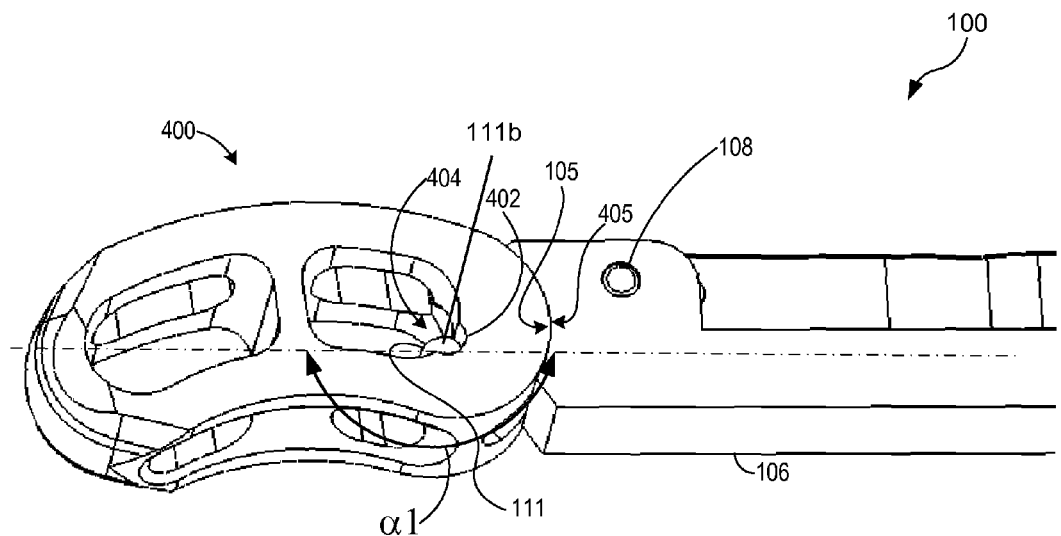
FIG. 5A illustrates an oblique view of the distal end of the delivery instrument with the spacer attached and substantially linear with the delivery instrument.
Figure 5B:
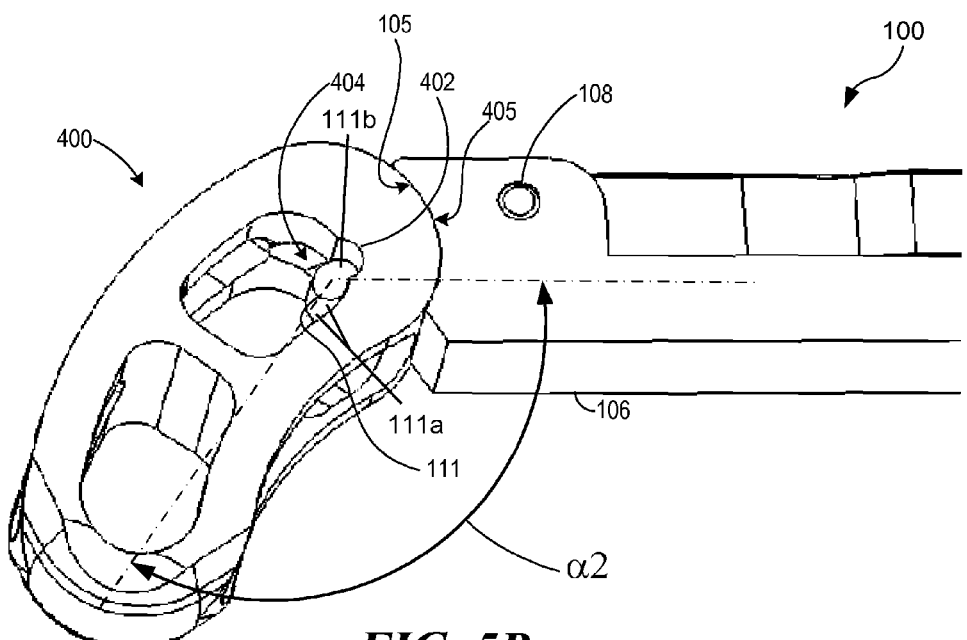
FIG. 5B illustrates an oblique view of the distal end of the delivery instrument with the spacer attached and rotated with regard to the delivery instrument.

Turning now to FIG. 5A, this figure illustrates an oblique view of the distal end of the delivery instrument 100 with the spacer 400 attached and in a relatively straight orientation with regard to the delivery instrument 100. FIG. 5B illustrates an oblique view of the distal end of the delivery instrument 100 with the spacer 400 attached and in a rotated orientation with regard to the delivery instrument 100. As shown in FIG. 5A the spacer 400 may be in a first position at an angle α1 with respect to the longitudinal axis of the delivery instrument 100. As shown in FIG. 5B the spacer 400 may be in a second position at an angle α2 with respect to the longitudinal axis of the delivery instrument 100.

In either of the first position (FIG. 5A) or the second position (FIG. 5B), the seating surfaces 405 of the insert 400 slidably contact the seating surfaces 105 of the main body 106 (only one set of seating surfaces 405 and 105 can be easily seen in this view). The connecting member 111 may be configured to attach the spacer 400 to the delivery instrument 100. The engagement recess 402 may enable the arms of the connecting member 111 of the engagement member 110 to securely and pivotally engage the spacer 400. In some embodiments, the arms of the connecting member 111 of the engagement member 110 may attach to the spacer 400 by sliding into the engagement recess 402. In other embodiments, the connecting member 111 may be inserted into an interior portion of the spacer 400 via the insertion port 404.

As seen in the second position (FIG. 5B), the rotation of the insert 400 may occur about a central axis defining the arms of the connecting member 111. The corresponding arcuate shapes of the seating surface 405 of the insert 400 and the seating surface 105 of the main body 106, as well as, the corresponding arcuate shapes of the arms of the connecting member 111 and the engagement recess 402, may facilitate the rotation or articulation of the insert 400. The seating surfaces 405 and the seating surfaces 105 may also at least partially function as cam surfaces defining the rotation of the insert 400 as the insert 400 is articulated. The rotation may be effectively inhibited or controlled by increasing the frictional forces developed between the seating surfaces 105, 405, through, for example, the tightening of the engagement knob 116 against the main body 106 (see FIG. 3). The tightening of the engagement knob 116 may clamp the insert 400 between the arms of the connecting member 111 and the seating surfaces 105. This clamping force may be increased during insertion of the insert 400 in order to more effectively transfer any impact force applied to an end of the delivery instrument 100. Additionally, the clamping force may be increased or decreased to facilitate or inhibit the rotation of the insert 400 relative to the delivery instrument 100.

Figure 5C:
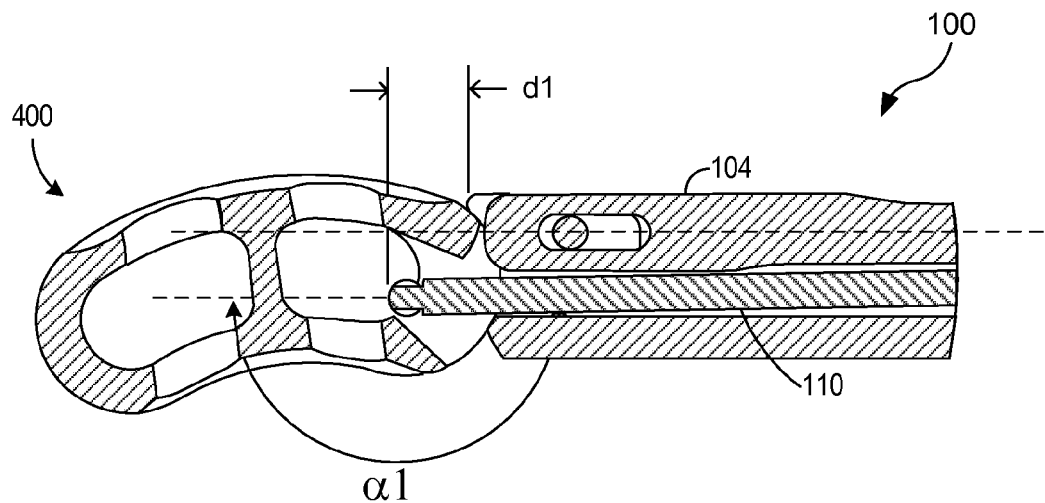
FIG. 5C illustrates an enlarged cross-sectional view of the delivery instrument of FIG. 1 with the spacer in a straight position relative to the delivery instrument.
Figure 5D:
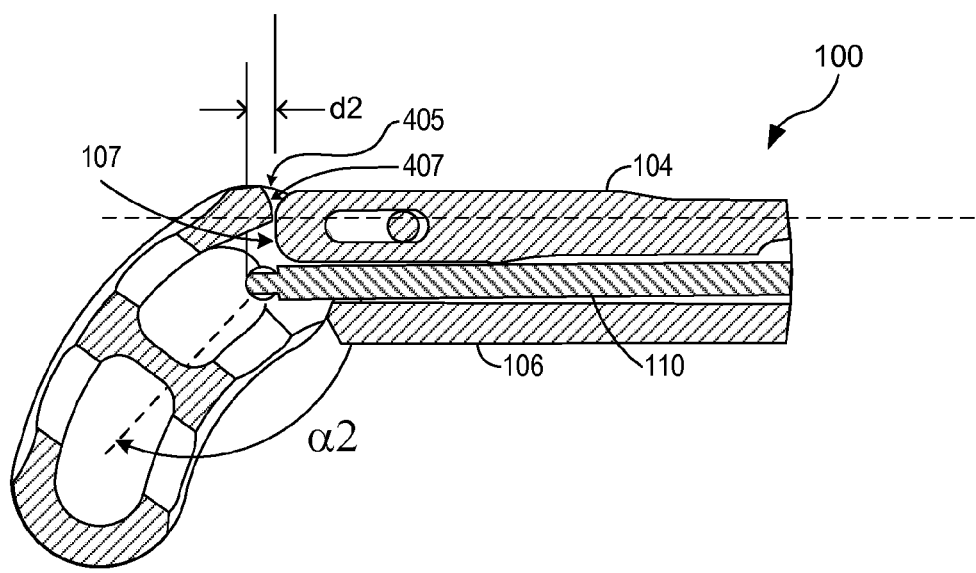
FIG. 5D illustrates an enlarged cross-sectional view of the delivery instrument of FIG. 1 with the spacer in a rotated position relative to the delivery instrument.

As more clearly shown in FIGS. 5C-5D, the delivery instrument 100 may articulate the spacer 400 about a center of rotation located inside of the spacer 400. Consequently it is the spacer 400, instead of the delivery instrument 100, which undergoes the substantial majority of articulation. In some embodiments, the center of rotation may be at the radial center of the outer radius defining the seating surfaces 405 of an anterior end of the spacer 400. The center of the outer radius of the anterior end of the spacer 400 may also correspond to the radius defining the seating surface 105 of the body 106 (i.e., a sliding abutment surface for the spacer 400). In other embodiments, the spacer 400 may rotate about a central axis defining the arms of the connecting member 111 (or the central axis defining the engagement recess 402).

The axis of the articulating member 104 and the axis of the engagement member 110 (both represented by broken lines in FIGS. 5C and 5D) may be offset from each other. Therefore, when the abutment surface 107 of the articulating member 104 engages an abutment surface 407 of the anterior end of the spacer 400, the spacer 400 may articulate about an appropriate center of rotation. The spacer 400 may transition from a relatively straight orientation, represented by angle "α1," to a rotated orientation represented by angle "α2." The rotation of the spacer 400 may be brought about by a translation of the articulating member 104 relative to the main body 106 as the articulating member 104 moves from a position represented by a distance "d1" (e.g., between the tip of the engagement member 110 to the abutment surface 107 of the pusher 104, see FIG. 5C), to a position represented by a distance "d2" (see FIG. 5D). Therefore, the delivery instrument 100 may rotate the spacer 400 without substantially rotating or physically moving the rest of the delivery instrument 100. One advantage that may arise from some embodiments of the present invention may be the ability to place the pivot point of the spacer 400 close to or co-incident with an instrument impact vector. This would allow for a more direct transfer of force from the proximal end of the instrument 100 through to the spacer 400. Another advantage of an embodiment configured as detailed above may be the facilitation of a more accurate placement of the spacer 400 between the vertebral plates.

The connecting member 111 of the engagement member 110 may secure the spacer 400 to the delivery instrument 100. After the spacer 400 is secured to the delivery instrument 100, the articulating member 104 may be moved with respect to the body 106, towards the spacer 400 (i.e., towards a distal end of the delivery instrument 100). The movement of the articulating member 104 may cause the abutment surface 107 of the articulating member 104 to engage an abutment surface 407 next to the elongated opening 406 on the spacer 400. The abutment surface 107 of the articulating member 104 may then press against the abutment surface 407 of the spacer 400. The forces developed between the abutment surfaces 107, 407, may result in a rotational movement of the spacer 400 about a central axis defining the engagement recess 402 or the origin of a radius defining the seating surface 405 of the anterior end of the spacer 400, for example. The body 106 may remain in substantially the same position while the articulating member 104 translates relative to and along the body 106. The translation of the articulating member 104 may be due to the operation of the articulating knob 114 (FIG. 3). In some embodiments, the longitudinal axis of the engagement member 110 may be offset from the point of contact between the abutment surfaces 107, 407.

In another illustrative embodiment, markings may be applied to the articulating member 104 and/or the body 106 so that the movement of the spacer 400 may be determined by viewing the relative positions of the markings on the articulating member 104 and/or the body 106. In some embodiments, the markings may be on the articulating knob 114. For example, the markings may refer to the degrees of rotation of the spacer 400 or the orientation of the spacer 400 relative to the delivery instrument 100. In this manner, the surgeon may ascertain the orientation of an in vivo spacer 400 during an operation. When the spacer 400 is in place, the surgeon may release the spacer 400 with an added assurance of proper positioning.

Figures 6A, 6B:
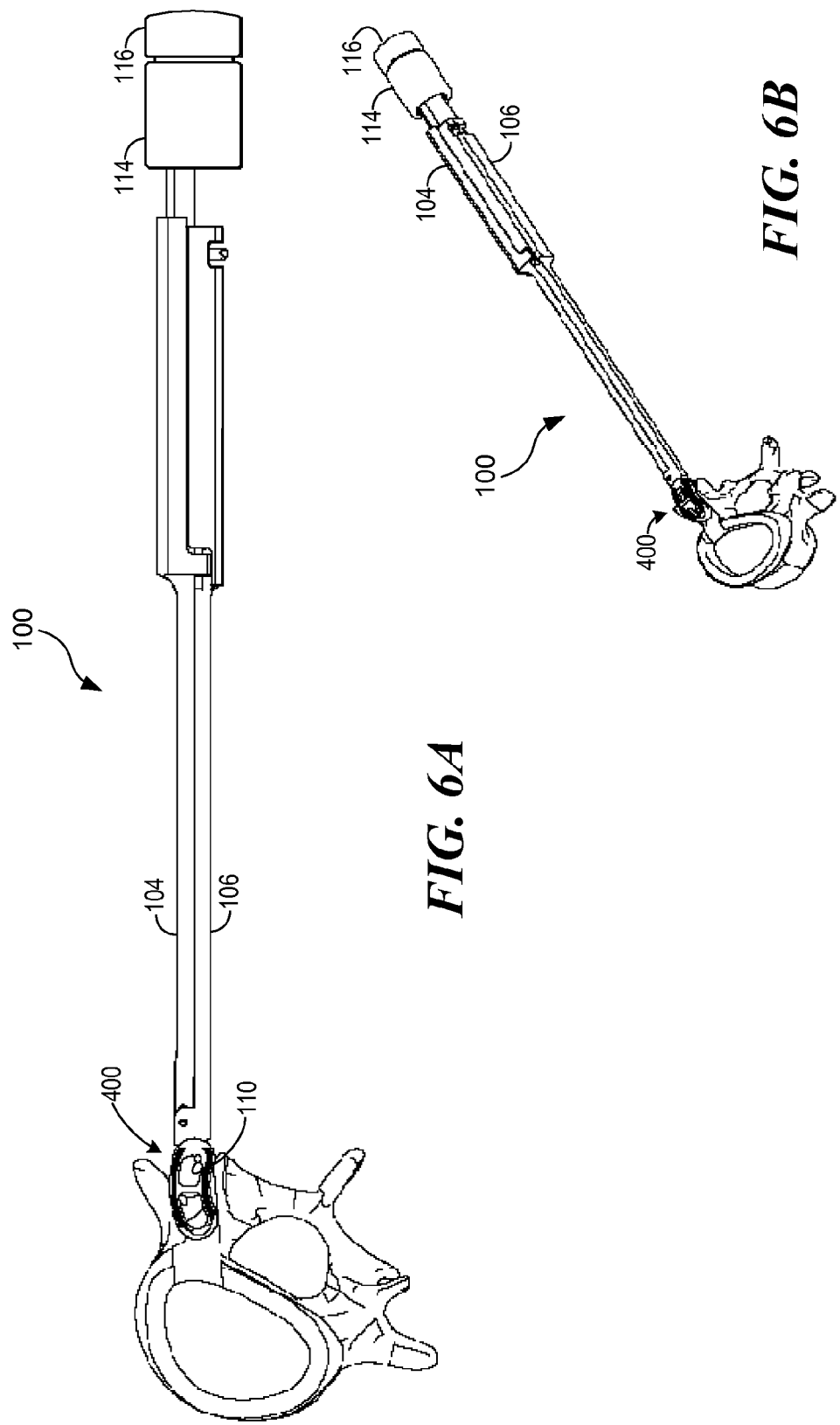
FIG. 6A illustrates a sagittal view of the delivery instrument of FIG. 1 and the spacer of FIG. 4, detailing the introduction of the spacer into an intervertebral space.
FIG. 6B illustrates an oblique view of the delivery instrument of FIG. 1 and the spacer of FIG. 4, detailing the introduction of the spacer into the intervertebral space.

Referring now to FIGS. 6A-9B, these figures illustrate the use of the delivery instrument 100 to insert a spacer 400 into an intervertebral space. More particularly, the figures illustrate the introduction of the spacer 400 into an intervertebral space (FIGS. 6A-6B), the proper placement of the spacer 400 (FIGS. 7A-7B), the release of the spacer 400 (FIGS. 8A-8B), and the removal of the delivery instrument 100 from the intervertebral space (FIGS. 9A-9B). FIGS. 6A and 6B illustrate the delivery instrument 100 securely holding the spacer 400, as the spacer 400 may be introduced into an intervertebral space. At this point in the procedure, the spacer 400 may be substantially in line with the longitudinal axis of the delivery instrument 100 and the spacer 400 may not have been articulated into an alternative orientation. The articulating member 104 may not have not been translated with respect to the main body 106. Therefore, the articulating knob 114 may be in an initial position.

The substantially straight orientation may be advantageous, in part, because a line of impact may pass relatively directly through the delivery instrument 100 and into the spacer 400. A surgeon attempting to force the spacer 400 between adjacent vertebrae of the intervertebral space may apply an impact force to the proximal end of the delivery instrument 100 in order to place the insert 400 within the intervertebral space. In order to secure the insert 400 against the delivery instrument 100 so as to more efficiently transfer the impact force, the engagement knob 116 may be rotated (e.g., tightened) to draw the engagement member 110 in a proximal direction, substantially fixing the position of the insert 400 and creating a relatively rigid structure.

FIGS. 7A and 7B illustrate the articulation of the spacer 400 relative to the delivery instrument 100. Once the spacer 400 enters the intervertebral space, the surgeon may articulate the spacer 400 by rotating the articulation knob 114. Rotating the articulation knob 114 may translate the articulation knob 114 along and relative to the main body 106. Since the articulation knob 114 may be fixed in a longitudinal direction with respect to the articulating member 104, translation of the articulation knob 114 may result in a corresponding translation of the articulating member 104 along and relative to the main body 106 (e.g., as indicated by the separation of the articulation knob 114 and the engagement knob 116 shown in the figure). An embodiment of the present invention may be configured such that one or more of the components of the delivery instrument 100 (e.g., the articulating member 104, the main body 106, the articulation knob 114, among others) may further comprise a scale to represent the orientation of the spacer 400 relative to the delivery instrument 100 within the intervertebral space. In some cases, it may be necessary to loosen the engagement knob 116 in order to facilitate the rotation of the articulating knob 114.

FIGS. 8A and 8B illustrate a point in which the engagement knob 116 has been rotated prior to releasing the spacer 400 from the delivery instrument 100 via the engagement member 110. The engagement member 110 may have been translated relative to the main body 106. Within the spacer 400, the arms of the connecting member 111 of the engagement member 110 may move in a distal direction relative to the spacer 400, disengaging the connecting member 111 from the spacer 400. The engagement lever 112 may be rotated through approximately 90°, correspondingly rotating the arms of the connecting member 111 relative to the spacer 400, as seen in FIG. 8A within the spacer 400.

However, up until the release and withdrawal of the delivery instrument 100 from the spacer 400, the spacer 400 may be withdrawn from the intervertebral space by rotating the engagement lever 112 and re-engaging the arms of the connecting member 111 with the spacer 400. The engagement knob 116 may be tightened and the spacer 400 secured to the delivery instrument 100. The delivery instrument 100 and the attached spacer 400 may then be withdrawn from the intervertebral space. Therefore, if a surgeon is unsatisfied with the placement or orientation of the spacer 400, or otherwise wishes to abort the procedure, an embodiment of the present invention may enable the surgeon to do so.

FIGS. 9A and 9B illustrate the beginning of the withdrawal of the delivery instrument 100 from the intervertebral space. As shown in FIGS. 8A and 8B, once a surgeon is satisfied with the placement and the orientation of the spacer 400, the surgeon may loosen the engagement knob 116 and rotate the engagement member 110 via the engagement lever 112. The arms of the connecting member 111 of the engagement member 110 may be substantially perpendicular to the engagement recess 402, but substantially parallel to the insertion port 404 and elongated opening 406 (see FIG. 4B). The surgeon may then withdraw the delivery instrument 100, thereby leaving the spacer 400 in a proper place and orientation.

Another Illustrative Embodiment

Turning now to FIGS. 10A and 10B, these figures illustrate a cross-sectional view of another illustrative embodiment of a delivery instrument 600 of the present invention designed to insert a spacer 700 into an intervertebral space, properly position it, and then release the spacer 700. FIG. 10A shows the spacer 700 attached to the delivery instrument 600 in a substantially straight orientation. FIG. 10B shows a view of the delivery instrument 600 and spacer 700 when the spacer 700 is in a rotated orientation. Some features of the illustrative embodiment shown in FIGS. 10A-10B may differ from the illustrative embodiment shown in FIGS. 5A-5B. In FIGS. 5A-5B the spacer 400 itself may articulate about the delivery instrument 100, while in FIGS. 10A-10B, a portion of the delivery instrument 600 (e.g., one or more grasping or attachment members 618, two grasping or attachment members 618 will be used for example in this illustrative embodiment) may articulate about the rest of the delivery instrument 600.

In the present illustrative embodiment, a main body 602 may be slidably coupled to a sliding actuator 606. The sliding actuator 606 may be configured to move with respect to the main body 602. A threaded knob 612 rotatably mounted on the delivery instrument 600 may couple the main body 602 to the sliding actuator 606. The threaded knob 612 may be rotated to move the sliding actuator 606 with respect to the main body 602. In some embodiments, the threaded knob 612 may comprise internal threads to threadably engage with a correspondingly threaded portion of the main body 602. The threaded knob 612 may also comprise an internal pin slot to slidably engage a pin 614. As a result, the pin 614 and the pin slot may fix the position of the sliding actuator 606 in the longitudinal direction with respect to the threaded knob 612.

The delivery instrument 600 may further comprise an internal actuator member 604 (detailed later). A handle or trigger 608 may be pivotably coupled to the main body 602. The trigger 608 may also be pivotably coupled to the actuator member 604 through the use of a link member 610. Therefore, the trigger 608 may be used to slidably move the actuator member 604 relative to the main body 602. The trigger 608 may also be used to maintain the actuator member 604 in a static or fixed position relative to the main body 602.

The distal end of the delivery instrument 600 may comprise an articulated joint 616. The articulated joint 616 may comprise a pivot pin 620 and grasping members 618. The grasping members 618 may be pivotally coupled to the sliding actuator 606 and the actuator member 604. As shown in FIG. 10B, when the sliding actuator 606 is moved towards the distal end of the delivery instrument 600, the articulated joint 616 may be rotated through an arc. The sliding actuator 606 may be moved with respect to the main body 602 due to the rotation of the threaded knob 612. The movement of the sliding actuator 606 may cause the grasping members 618 to pivot with respect to the main body 602. The articulated joint 616 may be rotated between at least a first position, represented by angle "$\alpha 3$," and a second position, represented by angle "$\alpha 4$." The rotation may result from the translation of the sliding actuator 606 between a position represented by a distance "d3" and a position represented by a distance "d4."

Figure 11:
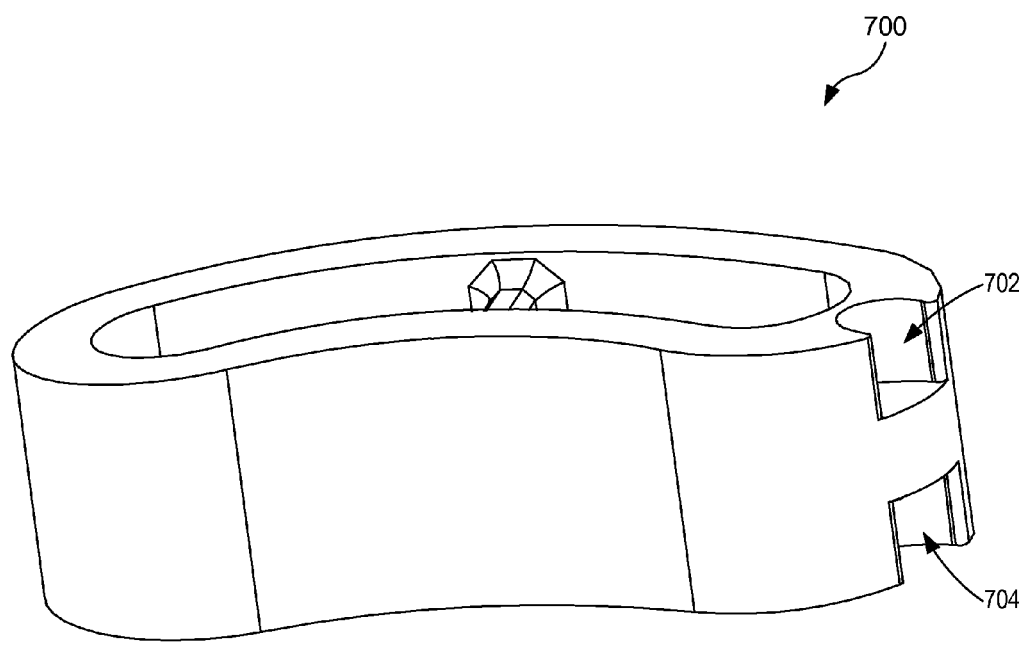
FIG. 11 illustrates an oblique view of another embodiment of a spacer designed to be inserted into the intervertebral space.

Referring now to FIG. 11, this figure shows an oblique view of a spacer 700 configured to be inserted into the intervertebral space. The spacer 700 may comprise a first grasping member recess 702. The spacer 700 may also comprise a second grasping member recess 704. The grasping recesses 702 and 704 are shown in this example as substantially cylindrical. However, the grasping recesses 702 and 704 may not be limited to this configuration. Any geometric configuration may be used, including configurations comprising straight or flat surfaces. The straight or flat surfaces may restrict the rotation of the spacer 700 relative to the grasping members 618 (FIGS. 10A-10B). In addition, the first grasping member recess 702 may not be similar to the second grasping member recess 704. As long as the specific grasping member recess 702, 704, corresponds to the respective grasping member 618, a variety of configurations may be used. The grasping members 618 may engage the spacer 700 by correspondingly sliding into the first grasping member recess 702 and the second grasping member recess 704. In some embodiments of the present invention, the grasping members 618 may be resiliently biased toward each other. Consequently, the grasping members 618 may naturally apply a clamping force to the spacer 700 there between.

Turning now to FIGS. 12A-12D, FIG. 12A illustrates a side view of the delivery instrument 600 with the spacer 700 attached. The grasping members 618 may be securely coupled to the spacer 700. As a result, the grasping members 618 may retain the spacer 700 while the spacer 700 is inserted into an intervertebral space. FIG. 12B illustrates a bottom view of the delivery instrument 600 with the spacer 700 attached. As more clearly seen in this figure, first grasping member 618A may engage the first grasping member recess 702 of the spacer 700. Second grasping member 618B may engage the second grasping member recess 704.

FIG. 12C illustrates an enlarged detailed bottom view of the distal end of the delivery instrument 600 with the spacer 700 attached, as shown in FIG. 12B. The spacer 700 may be retained by the grasping members 618A, 618B respectively engaging the first grasping member recess 702 and the second grasping member recess 704. Additionally, the internal actuator member 604 may comprise a wedging portion 640. The wedging portion 640 may interact with the grasping members 618A, 618B to secure and release the spacer 700. The interaction of the wedging portion 640 will be described in greater detail with reference to FIGS. 13A-13D.

FIG. 12D illustrates a cross-sectional view of the distal end of the delivery instrument 600 with the spacer 700 attached as shown in FIG. 12C and viewed along line 12D-12D. This cross-sectional view illustrates the articulated joint 616 in greater detail. Each grasping member 618 may comprise a circular portion 624, a thumb portion 628, and an extended finger portion 630. Further, a short compressive spring 643 (See FIG. 15B), Belleville washer, or other resilient device, for example, may be inserted between each of the grasping members 618 and the main body portion 602. The springs 643 may resiliently bias the grasping members 618 towards one another. Consequently, the springs 643 may resiliently bias the grasping members 618 against an attached spacer 700, thereby causing the grasping members 618 to apply a clamping force to a spacer 700 located there between.

A pin 626 may pivotally couple the thumb portion 628 of a grasping member 618 to a sliding actuator 606. The internal actuator member 604 may be adjacent to a first end of the extended finger portion 630, within close proximity to the pivot pin 620. The spacer 700 may be attached at a second end of the extended finger portion 630. The pivot pin 620 may pivotally couple the grasping members 618 to the main body 602. The circular portion 624 may define a specific arc through which the grasping members 618 may articulate the spacer 700. Accordingly, as the sliding actuator 606 moves relative to the main body 602, the thumb portion 628 may articulate through an arc that may be dependent upon the circular portion 624. The movement of the thumb portion 628 may lead to corresponding movement of the extended finger portion 630. Movement of the extended finger portion 630 may lead to corresponding movement of the spacer 700. Therefore, movement of the thumb portion 628 due to interaction with the sliding actuator 606 may result in an articulating movement of the spacer 700.

Figure 13A:
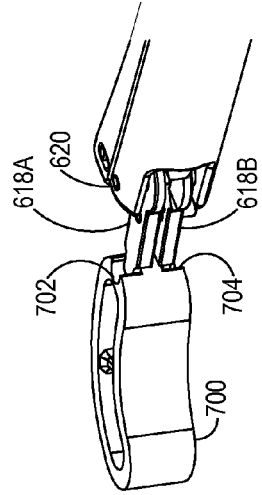
FIGS. 13A-13B illustrate oblique views of the distal end of the delivery instrument of FIG. 12A with the spacer attached, prior to the delivery instrument releasing the spacer.
Figure 13B:
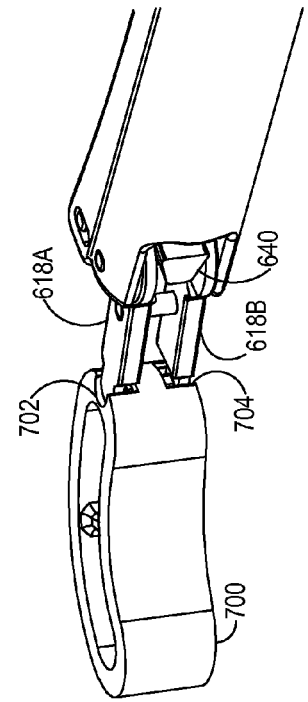
Figure 13C:
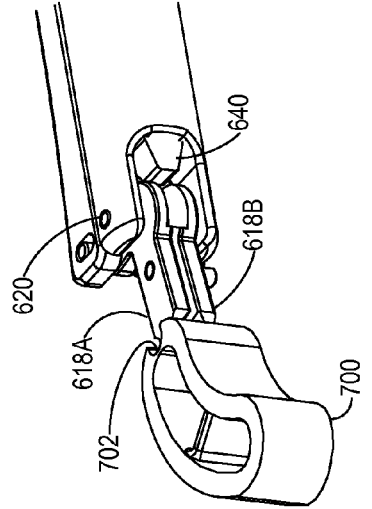
FIGS. 13C-13D illustrate oblique views of the distal end of the delivery instrument of FIGS. 13A-13B along with the spacer, when the delivery instrument releases the spacer.
Figure 13D:
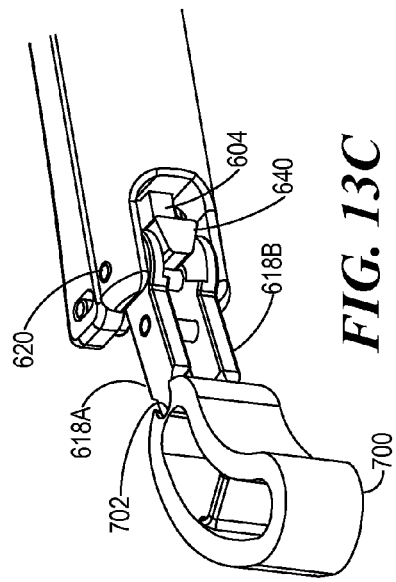

Referring now to FIGS. 13A-13D, these figures show oblique views of the distal end of the delivery instrument 600 with the spacer 700 attached. The delivery instrument 600 may be configured to allow a surgeon to properly position the spacer 700 while manipulating the delivery instrument 600. Once the spacer 700 is properly positioned, the surgeon may then release the spacer 700. FIGS. 13A-13B show oblique views of the delivery instrument 600 in which the grasping members 618A and 618B may be coupled or attached to the spacer 700. FIGS. 13C-13D show oblique views of the delivery instrument 600 in which the grasping members 618A and 618B may be oriented to release the spacer 700. Accordingly, when the surgeon has positioned the spacer 700 in an appropriate position within the intervertebral space, then the delivery instrument 600 may be operated to release the spacer 700. The delivery instrument 600 may then be withdrawn from the intervertebral space.

As shown in FIGS. 13A-13B, the first grasping member 618A and the second grasping member 618B may be positioned proximate to one another. The first grasping member 618A may be positioned to connect to the first grasping member recess 702. The second grasping member 618B may be positioned to connect to the second grasping member recess 704. As more clearly seen in FIG. 12A, the wedging portion 640 of the actuator member 604 (FIGS. 12C-12D) may be located adjacent to the grasping members 618A, 618B. As shown in these figures, the wedging portion 640 may be withdrawn from the first and second grasping members 618A, 618B. The first grasping member 618A and the second grasping member 618B may be resiliently biased towards one another along an axis of the pivot pin 620 so that they may exert a clamping force upon the spacer 700.

As shown in FIGS. 13C-13D, the wedging portion 640 may be manipulated to be inserted between the first grasping member 618A and the second grasping member 618B. The wedging portion 640 may be slidably engaged with each of the first and second grasping members 618A, 618B. The engagement of the wedging portion 640 with the first and second grasping members 618A, 618B may counteract the resilient bias applied to the members (for example) and force the first and second grasping members 618A, 618B apart from one another along an axis of the pivot pin 620. The wedging portion 640 may be moved into and out of engagement with the first and second grasping members 618A, 618B by the actuator member 604. Translating the actuator member 604 so as to move the wedging portion 640 into and out of position may release and attach the first and second grasping members 618A, 618B and the spacer 700.

As previously described, movement of the actuator member 604 may slidably force the wedging portion 640 between the grasping members 618A, 618B. The movement of the actuator member 604 may be controlled by an operating member, the operating member may include a trigger 608 (FIGS. 10A-10B) in combination with the link member 610 (FIGS. 10A-10B). This action may force the first and second grasping members 618A, 618B to separate from each other, moving between a position in which the first and second grasping members 618A, 618B engage the spacer 700, and a position in which the first and second grasping members 618A, 618B release the spacer 700.

Turning now to FIGS. 14A-14B, these figures illustrate an engaged position in which the first and second grasping members 618A, 618B of the delivery instrument 600 are biased against the spacer 700 by the springs 643 at an approximate distance "h1" apart. The springs 643 may be provided between opposing surfaces at the distal end of the main body 602 and the first and second grasping members 618A, 618B. The delivery instrument 600 may further comprise a stop pin 645 to help align and control the grasping members 618A, 618B as they move toward one another substantially along the axes of the pivot pin 620 and the stop pin 645. When the delivery instrument 600 may be holding the spacer 700, as shown in these figures, the wedging portion 640 at the distal end of the actuator member 604 may be proximate to the first and second grasping members 618A, 618B.

Referring now to FIGS. 15A, 15B, these figures show a released position in which the delivery instrument 600 may be released or separated from the spacer 700. The wedging portion 640 at the end of the actuator member 604 may advanced between the opposing first and second grasping members 618A, 618B. As the slanted surfaces of the wedging portion 640 slidingly engage the first and second grasping members 618A, 618B, the first and second grasping members 618A, 618B may be forced apart, against the bias of the resilient springs 643, to an approximate distance "h2." While the first and second grasping members 618A, 618B may be moving apart, the first and second grasping members 618A, 618B may be guided along the axes of the stop pin 645 and the pivot pin 620. Additionally, the stop pin 645 may engage the first and second grasping members 618A, 618B so that the separation between the first grasping member 618A and the second grasping member 618B may be limited to a user selectable amount. In some embodiments of the present invention, the maximum separation amount for the outer surfaces of the first and second grasping members 618A, 618B may be less than the thickness of the spacer 700 to reflect the space constraints imposed by the intervertebral space surrounding an installed spacer 700.

The separation of the first grasping member 618A from the second grasping member 618B may detach the delivery instrument 600 from the spacer 700. After the delivery instrument 600 is detached from the spacer 700, the delivery instrument 600 may be removed from the intervertebral space and the patient without requiring or causing a substantial alteration in the position or orientation of the installed spacer 700. Similarly, the wedging portion 640 may also be operated in a reverse manner to initially grasp the spacer 700.

In some embodiments, markings may be applied to the sliding actuator 606 and/or the main body 602, for example, so that the orientation of the spacer 700 may be indicated by viewing the optional markings on the sliding actuator portion 606 and/or the main body portion 602. Alternatively or in addition to, the markings may be on the threaded knob 612 (FIG. 10A). These markings may refer to the degrees of rotation of the spacer 700 relative to the delivery instrument 600 or to the position and orientation of the spacer 700. As a result, the surgeon may be able to more quickly and accurately position and orient the spacer 700 during an operation.

Another Illustrative Embodiment

Figure 16C:
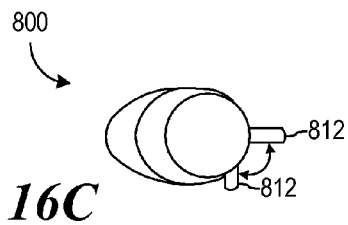
FIG. 16C illustrates an end view of the instrument of FIG. 16A, detailing the rotation of the engagement lever of the instrument of FIG. 16A.
Figure 16A:
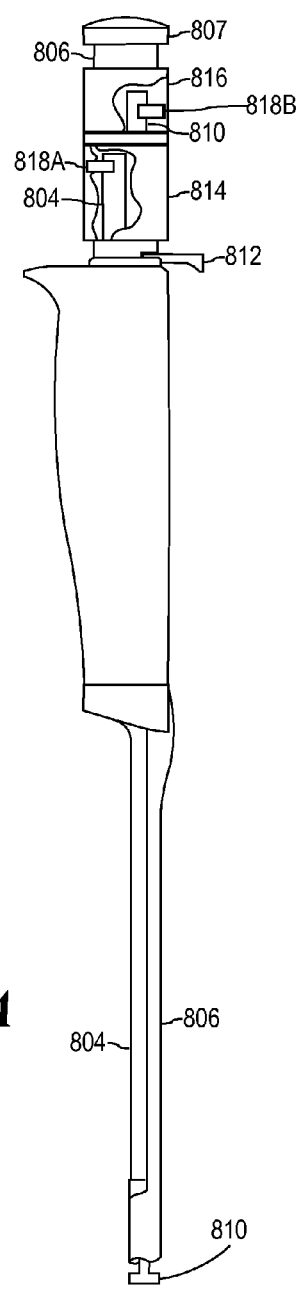
FIG. 16A illustrates a wire frame, side view of another embodiment of a delivery instrument designed to insert a spacer into the intervertebral space.
Figure 16B:
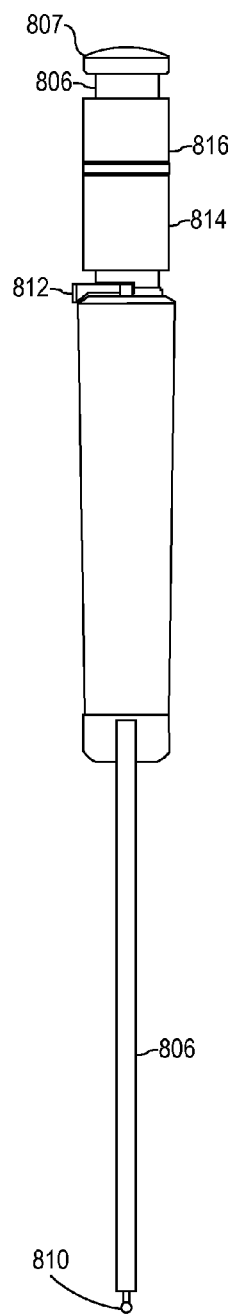
FIG. 16B illustrates a wire frame, top view of the instrument of FIG. 16A.

In another illustrative embodiment of the present invention, as illustrated in FIGS. 16A-16C, the delivery instrument 800 may comprise an actuator 804, main body 806, end cap 807, and an engagement member 810. The main body 806 may be slidably coupled to the actuator 804 such that the actuator 804 may translate relative to the main body 806. The delivery instrument 800 may further comprise an engagement lever 812, a first articulation knob 814, a second articulation knob 816, and pins 818A, 818B. The first articulation knob 814 may be fixed in position in a longitudinal direction with respect to the actuator 804 via pin 818A. The second articulation knob 816 may be fixed in position in a longitudinal direction with respect to the engagement member 810 via pin 818B. The first articulation knob 814 and the second articulation knob 816 may be rotatably and threadably engaged with corresponding threads on a proximal end of the main body 806. The pins 818A and 818B may respectively be slidably engaged to the first articulation knob 814 and the second articulation knob 816.

Rotation of the first articulation knob 814 may translate the actuator 804 relative to the main body 806. Rotation of the second articulation knob 816 may translate the engagement member 810 relative to the main body 806. Translation of the actuator 804 may result in the rotation of an attached spacer (not shown in these figures). Translation of the engagement member 810 may loosen or tighten the attachment between a spacer and the main body 806. The engagement lever 812 may rotate the engagement member 810 about an axis substantially parallel to the longitudinal axis of the delivery instrument 800.

An extension of the main body (i.e., the main body 806) may extend beyond the proximal end of the second articulation knob 816. This extension of the main body 806 can pass through a suitable cavity in the articulation knob 816 and have an end cap 807 configured to be impacted in order to aid in the insertion of the spacer (not shown) into the intervertebral space. The main body 806 and end cap 807 may form a relatively continuous structural member that may efficiently and effectively transfer an impact force from the proximal surface of the end cap 807 to the distal surface of the main body 806. From the distal end of the main body 806, an impact may be transferred to an attached spacer.

Operation of the delivery instrument 800 is similar to the previously described embodiments. A spacer (not shown) may be attached through the engagement member 810 and rotation of the engagement lever 812. The spacer may then be secured against the main body 806 through the rotation of the second articulation knob 816. The spacer may be placed in position proximate to an intervertebral space. The end cap 807 may be impacted to force the spacer within the intervertebral space. The first articulation knob 814 may then be rotated in order to properly orient and position the spacer within the intervertebral space through the translations of the actuator 804. If needed, the second articulation knob 816 may be slightly loosened in order to facilitate the articulation of the spacer within the intervertebral space. Once correctly positioned, the second articulation knob 816 may be loosened and the engagement lever 812 rotated through approximately 90°. The spacer will be released from the distal end of the delivery instrument 800 and the delivery instrument may be removed from the intervertebral space.

In this illustrative embodiment of the present invention the end cap 807 or pad may be applied directly to or integral with the main body 806, so that an impact is transferred directly to the spacer through the main body 806. Accordingly, neither the first articulation knob 814 nor the second articulation knob 816 has the impact applied to the body of either knob. This embodiment may allow for a longer usable life of the delivery instrument 800 along with an increased accuracy of the articulation knobs 814, 816, due to the impact surface being transferred away from the articulation knobs 814, 816 to the end cap 807 or pad.

Another Illustrative Embodiment

Figures 17, 18:
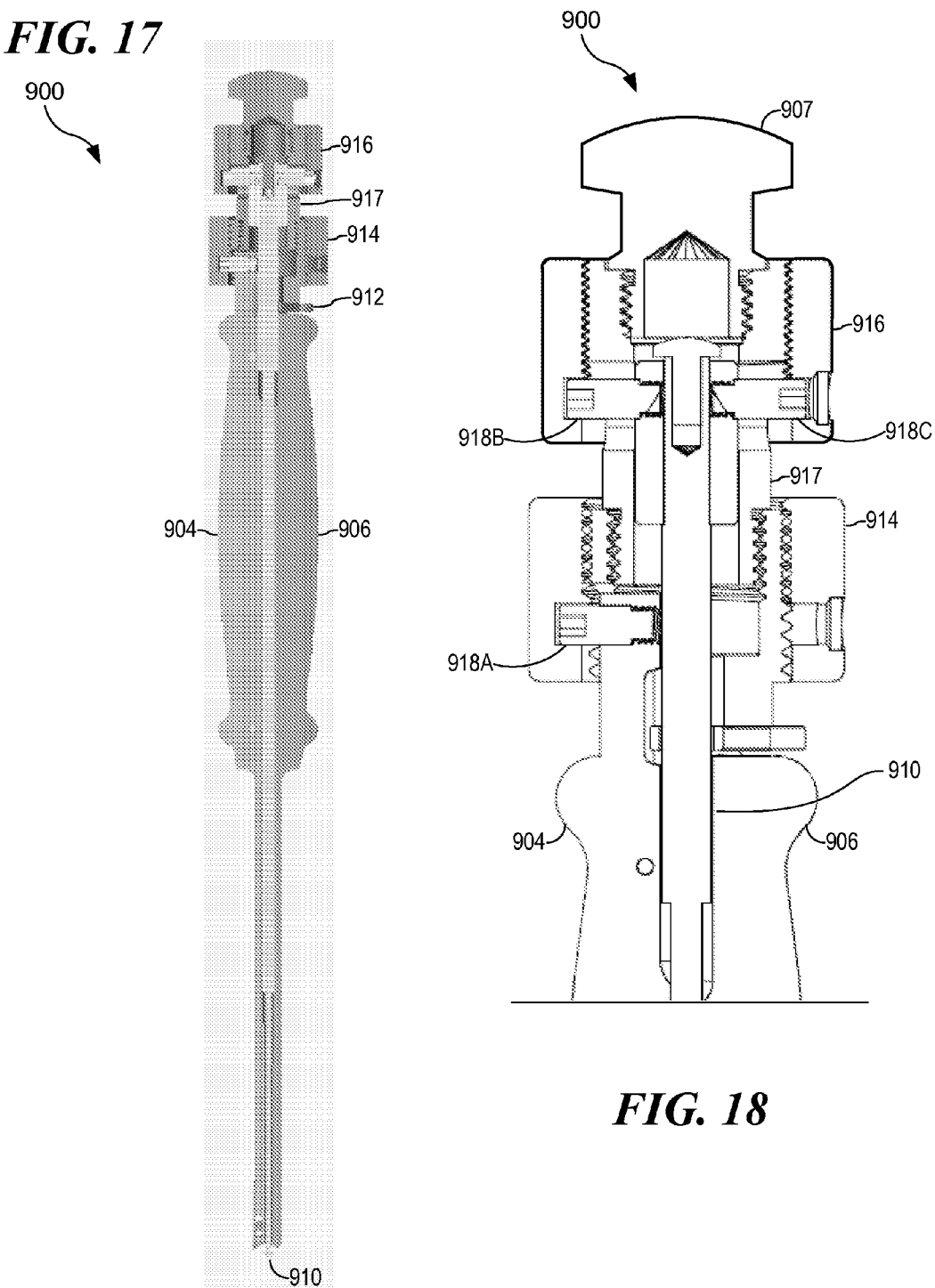
FIG. 17 illustrates a cross-sectional view of another embodiment of a delivery instrument designed to insert a spacer into the intervertebral space.
FIG. 18 illustrates an enlarged cross-sectional view of a proximal end of the instrument of FIG. 17.
Figure 19:
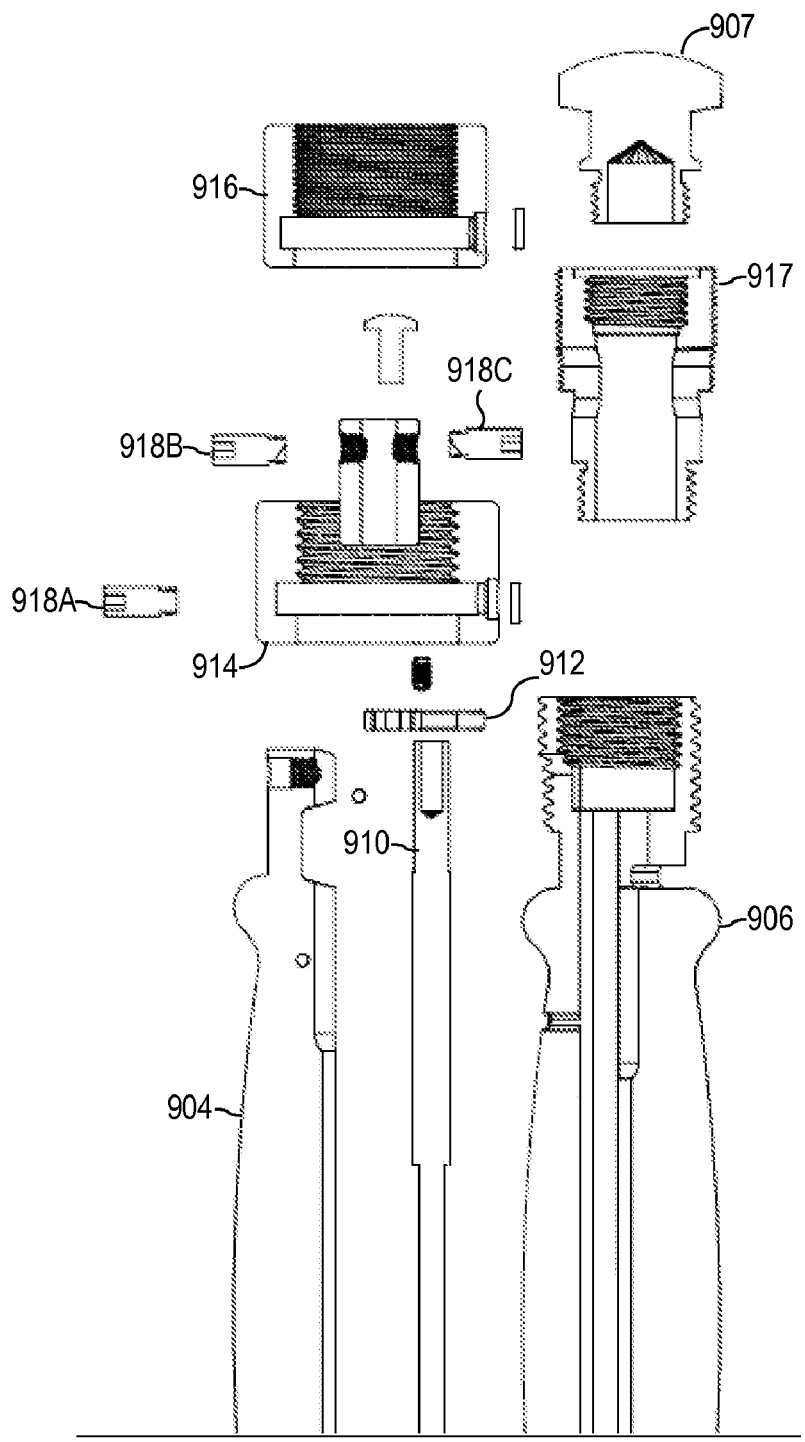
FIG. 19 illustrates an enlarged cross-sectional assembly view of a proximal end of the instrument of FIG. 17.

In another illustrative embodiment of the present invention, as illustrated in FIGS. 17-19, the delivery instrument 900 may comprise an actuator 904, main body 906, end cap 907, and an engagement member 910. The main body 906 may be movably coupled to the actuator 904 such that the actuator 904 may translate relative to the main body 906. The delivery instrument 900 may further comprise an engagement lever 912, a first articulation knob 914, a second articulation knob 916, and pins 918A, 918B, and 918C. The first articulation knob 914 may be fixed in position in a longitudinal direction with respect to the actuator 904 via pin 918A. The second articulation knob 916 may be fixed in position in a longitudinal direction with respect to the engagement member 910 via pins 918B and 918C. The first articulation knob 914 may be rotatably and threadably engaged with corresponding threads on a proximal end of the main body 906. The pin 918A may be slidably engaged to the first articulation knob 914. The pins 918B and 918C may be slidably engaged to the second articulation knob 916. However, as in other embodiments, the pins 918A, 918B, and 918C, may be respectively fastened to articulation knobs 914 and 916, and slidably engaged with the actuator 904 and engagement member 910.

Rotation of the first articulation knob 914 may translate the actuator 904 relative to the main body 906. Rotation of the second articulation knob 916 may translate the engagement member 910 relative to the main body 906. Translation of the actuator 904 may result in the rotation of an attached spacer (not shown in these figures). Translation of the engagement member 910 may loosen or tighten the attachment between a spacer and the main body 906. Two pins, 918B and 918C, may be used to transfer more of the force generated by the rotation of the second articulation knob 916 into the engagement member 910. The engagement lever 912 may rotate the engagement member 910 about an axis substantially parallel to the longitudinal axis of the delivery instrument 900.

An extension member 917 attached to the main body (i.e., the main body 806) may be accessed through the proximal end of the second articulation knob 916. This extension member 917, attached to the main body 806, can pass through a suitable cavity in the articulation knob 916 and have an end cap 907 configured to be impacted in order to aid in the insertion of the spacer (not shown) into the intervertebral space. The main body 906, extension member 917, and end cap 907 may form a relatively continuous structural member. This structural member may efficiently and effectively transfer an impact force from the proximal surface of the end cap 907 to the distal surface of the main body 906. From the distal end of the main body 906, an impact may be transferred to an attached spacer.

Turning now to FIG. 19, the relationship between the various components of an illustrative embodiment of the delivery instrument 900 may be easily seen. On the right side of the drawing, end cap 907, extension member 917, and main body 906 may substantially form the non-moving portion of the delivery instrument 900. The use of an extension member 917 is for aiding the assembly of the first and second articulation knobs 914, 916. Additionally, the end cap 907, extension member 917, and main body 906 may form a relatively rigid structure for transferring impact loads between a proximal end and a distal end. Since the various components are substantially fixed in relationship to one another, they may be configured for strength, as opposed to some of the moving members (e.g., articulation knobs 914, 916), which may need to be configured for accuracy. In addition, the three members (906, 907, and 917) may be repeatedly struck without directly applying a large portion of the impact loads to the moving components of the delivery instrument 900. This embodiment may allow for a longer usable life of the delivery instrument 900 along with an increased accuracy of the articulation knobs 914, 916, due to the impact surface being transferred away from the articulation knobs 914, 916 to the end cap 907 or pad.

Operation of the delivery instrument 900 is similar to the previously described embodiments. A spacer (not shown) may be attached through the engagement member 910 and rotation of the engagement lever 912. The spacer may then be secured against the main body 906 through the rotation of the second articulation knob 916. The spacer may be placed in position proximate to an intervertebral space. The end cap 907 may be impacted to force the spacer within the intervertebral space. The first articulation knob 914 may then be rotated in order to properly orient and position the spacer within the intervertebral space through the translations of the actuator 904. If needed, the second articulation knob 916 may be slightly loosened in order to facilitate the articulation of the spacer within the intervertebral space. Once correctly positioned, the second articulation knob 916 may be loosened and the engagement lever 912 rotated through approximately 90°. The spacer will be released from the distal end of the delivery instrument 900 and the delivery instrument may be removed from the intervertebral space.

Alternative Embodiments

It is understood that multiple embodiments can take many forms and configurations. Accordingly, several variations of the present design may be made without departing from the scope of this disclosure. The capabilities outlined herein allow for the possibility of a variety of delivery instruments. This disclosure should not be read as preferring any particular delivery instrument, but is instead directed to the underlying concepts on which these delivery instruments can be built. For example, as illustrated in FIG. 20, any type of mechanism 10 (e.g., gears, sliders, electromechanical actuators) may be used to rotate the spacers 11 of certain embodiments of the present invention when they may be coupled to an instrument 12.

Having thus described specific embodiments, it is noted that the embodiments disclosed herein are illustrative rather than limiting in nature. A wide range of variations, modifications, changes, and substitutions are contemplated in the foregoing disclosure. In addition, in some instances, some features may be employed without a corresponding use of other features. Many such variations and modifications may be considered desirable by those skilled in the art based upon a review of the foregoing description of embodiments. Accordingly, it is appropriate that the appended claims be construed broadly and in a manner consistent with the scope of these embodiments.

This invention claims:

1. A medical instrument for placing an insert in a space between boney structures, said instrument comprising:
   a body;
   an engagement member rotatably coupled to said body and configured to releasably hold an insert, said engagement member rotatable in a first plane of rotation relative to said body;
   an articulating member coupled to said body for translation relative to said body and to said engagement member and adapted to rotate, in a second plane of rotation transverse to said first plane of rotation, the insert held by said engagement member relative to said body in response to the translation;
   an articulator operatively coupled to said articulating member;
   wherein actuating said articulator translates said articulating member relative to said body and to said engagement member to rotate, in said second plane of rotation, the insert held by said engagement member relative to said body in response to the translation; and
   wherein said articulator comprises a rotating member configured to rotate about said body.

2. The medical instrument of claim 1 wherein said engagement member further comprises
   a cross-member at a distal end of a first portion of said engagement member,
   wherein said cross-member rotatively engages a corresponding recess provided in the insert, and
   wherein said cross-member is configured to rotate in said first plane of rotation about
   a longitudinal axis of said first portion of said engagement member.

3. The medical instrument of claim 2, wherein said cross-member comprises a substantially arcuate cross-section.

4. The medical instrument of claim 2, wherein at least a portion of the perimeter of said cross-member comprises a substantially arcuate cross-section.

5. The medical instrument of claim 2, wherein said cross-member comprises an arm extending outward from said first portion.

6. The medical instrument of claim 5, wherein said cross-member further comprises a second arm extending outward from said first portion.

7. The medical instrument of claim 2, wherein said cross-member comprises a slanted portion angled with respect to said axis of said first portion.

8. The medical instrument of claim 1, wherein said articulator is threadably engaged with said body and fixed in a first direction relative to said articulating member.

9. The medical instrument of claim 1, wherein said rotating member comprises a knob.

10. The medical instrument of claim 8, wherein said articulator is fixed to said articulating member via a pin and groove engagement.

11. The medical instrument of claim 8, wherein said articulator is fixed to said articulating member via a pin coupled with a groove,
   wherein said pin is attached to said articulating member and said groove is provided with said articulator.

12. The medical instrument of claim 1, wherein said engagement member further comprises a release member.

13. The medical instrument of claim 12, wherein actuating said release member rotates said engagement member relative to said body.

14. The medical instrument of claim 1, further comprising an end cap integrated with a proximal end of said body.

15. The medical instrument of claim 1, wherein said body further comprises a seat at a distal end configured to engage an end of the attached insert.

16. A system comprising:
   an insert further comprising an arcuate end surface, an engagement recess provided inside of said insert, and an insertion slot providing access to said engagement recess;
   a delivery device further comprising:
      a body;
      an engagement member rotatably coupled to said body and configured to releasably hold said insert, said engagement member rotatable in a first plane of rotation relative to said body; and
      an articulating member coupled to said body for translation relative to said body and to said engagement member and adapted to rotate, in a second plane of rotation transverse to said first plane of rotation, said insert held by said engagement member relative to said body in response to the translation;
wherein an end of said engagement member is rotatably coupled to said engagement recess of said insert;
wherein said arcuate end surface of said insert abuts an end of said body and is configured to facilitate the camming of said insert in said second plane of rotation relative to said body in response to the translation of said articulating member relative to said body.

* * * * *